US009493844B2

(12) United States Patent
Sastry-Dent et al.

(10) Patent No.: US 9,493,844 B2
(45) Date of Patent: Nov. 15, 2016

(54) DNA DETECTION METHODS FOR SITE SPECIFIC NUCLEASE ACTIVITY

(71) Applicant: Dow AgroSciences LLC, Indianapolis, IN (US)

(72) Inventors: Lakshmi Sastry-Dent, Indianapolis, IN (US); Matthew Simpson, Brownsburg, IN (US); Zehui Cao, Westfield, IN (US); Wei Chen, Carmel, IN (US); Ning Zhou, Zionsville, IN (US); Steven R. Webb, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 43 days.

(21) Appl. No.: 14/105,223

(22) Filed: Dec. 13, 2013

(65) Prior Publication Data

US 2014/0298547 A1 Oct. 2, 2014

Related U.S. Application Data

(60) Provisional application No. 61/736,856, filed on Dec. 13, 2012.

(51) Int. Cl.
*C12Q 1/68* (2006.01)

(52) U.S. Cl.
CPC ........... *C12Q 1/6895* (2013.01); *C12Q 1/6858* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,481,266 B2 | 7/2013 | Shao et al. | |
| 2004/0268442 A1 | 12/2004 | Miller et al. | |
| 2006/0070139 A1* | 3/2006 | Bing et al. | 800/279 |
| 2006/0282915 A1* | 12/2006 | Malven et al. | 800/278 |
| 2007/0136836 A1* | 6/2007 | Arnevik | A01H 1/02 800/278 |
| 2007/0261129 A1 | 11/2007 | Andersen et al. | |
| 2008/0182332 A1 | 7/2008 | Cai et al. | |
| 2009/0081681 A1* | 3/2009 | Edmonds et al. | 435/6 |
| 2009/0131272 A1* | 5/2009 | Parinov et al. | 506/10 |
| 2009/0136532 A1 | 5/2009 | Webb et al. | |
| 2009/0210970 A1 | 8/2009 | Hondred et al. | |
| 2011/0294675 A1 | 12/2011 | Brabetz et al. | |
| 2012/0282624 A1 | 11/2012 | Han et al. | |

FOREIGN PATENT DOCUMENTS

| | | |
|---|---|---|
| CN | 101123871 A | 2/2008 |
| CN | 101434988 A | 5/2009 |
| CN | 101578111 A | 11/2009 |
| CN | 102816783 A | 12/2012 |
| WO | 2007133732 A2 | 11/2007 |

OTHER PUBLICATIONS

Merriam-Webster (definition of "proximal," attached, available at http://www.merriam-webster.com/dictionary/proximal, accessed Aug. 20, 2015).*
Merriam-Webster (definition of "indicate," attached, available at http://www.merriam-webster.com/dictionary/indicate, accessed Aug. 20, 2015).*
Mao et al. (Characterization of EvaGreen and the implication of its physicochemical properties for qPCR applications, BMC Biotechnol. 2007; 7: 76, Published online Nov. 9, 2007).*
Carroll (A CRISPR Approach to Gene Targeting, Mol Ther. Sep. 2012;20(9):1658-60).*
Cai, C. Q. et al, Targeted transgene integration in plant cells using designed zinc finger nucleases; Plant Mol. Biol. 69, pp. 699-709 (2008).
Shukla, V. K. et al, Precise genome modification in the crop species *Zea mays* using zinc-finger nucleases, Nature, May 21 vol. 459; 437-441 (2009).
Iida, S. & Terada, R., Modification of endogenous natural genes by gene targeting in rice and other higher plants. Plant Mol. Biol. 59, 205-219 (2005).
Wright, D. A. et al, High-frequency homologous recombination in plants mediated by zinc-finger nucleases, Plant Journal 44, 693-705 (2005).
Lloyd, A. et al, Targeted mutagenesis using zinc-finger nucleases in Arabidopsis, Proc Natl Acad. Sci. USA, 102, 2232-2237 (2005).
Porteus, Mammalian Gene Targeting with Designed Zinc Finger Nucleases, Molecular Therapy, vol. 13, No. 2, pp. 438-446 (2005).
Curtin, S. J., et al, Genome engineering of crops with designer nucleases. The Plant Genome, 5(2). 42-50 (2012).
Ravi, V. et al, Establishment of PCR Laboratory in Developing Countries. World Health Organization Regional Office for South-East Asia, 2011.
Jones Prather, K.L., et al. Identification and Characterization of IS1 transposition in plasmid amplification mutants of *E. coli* clones producing DNA vaccines. Appl Microbiol Biotechnol, vol. 73; 815-826 (2006).
James, D., et al., Reliable Detection and Identification of Genetically Modified Maize, Soybean, and Canola by Multiplex PCR Analysis, Journal of Agricultural and Food Chemistry, 2003, 5829-5834, 51;20.

* cited by examiner

*Primary Examiner* — Aaron Priest
(74) *Attorney, Agent, or Firm* — Sean M. Russell; James Daly, IV

(57) ABSTRACT

The present disclosure provides methods for detecting and identifying plant events that contain precision targeted genomic loci, and plants and plant cells comprising such targeted genomic loci. The method can be deployed as a high throughput process utilized for screening the intactness or disruption of a targeted genomic loci and optionally for detecting a donor DNA polynucleotide insertion at the targeted genomic loci. The methods are readily applicable for the identification of plant events produced via a targeting method which results from the use of a site specific nuclease.

20 Claims, 14 Drawing Sheets

Figure 5

| Event | Copy # PAT v9 | ZFN Disruption | 5' PCR | 3' PCR | TI |
|---|---|---|---|---|---|
| 105906/107855/029-082 | 1.1 | + | + | + | + |
| 105906/107855/057-265 | 2.5 | + | + | + | + |
| 105906/107855/057-339 | 5.0 | + | + | + | + |
| 105906/107855/058-274 | 2.5 | + | + | + | + |
| 105906/107855/060-807 | 2.5 | + | + | + | + |
| 105906/107855/061-579 | 7.3 | + | + | + | + |
| 105906/107855/063-695 | 1.2 | + | - | + | + |
| 105906/107855/066-608 | 4.1 | + | - | - | + |
| 105906/107855/066-619 | 3.5 | + | - | - | + |
| 105906/107855/066-848 | 2.3 | + | + | + | + |
| 105906/107855/067-752 | 2.4 | + | + | + | + |
| 105906/107855/067-895 | 2.0 | + | - | - | + |
| 105906/107855/067-906 | 12.7 | + | - | - | + |
| 105906/107855/067-914 | 2.3 | + | + | + | + |
| 105906/107855/067-935 | 10.0 | + | - | - | + |
| 105906/107855/067-938 | 2.4 | + | + | + | + |

(a)

Fragment of pDAB105818
285 bp (molecule 18863 bp)

(b)

(a) 5' in-out (b) 3' in-out (a) Showing 25 of 4596 features for pDAB105821.1.295.1::pDAB105828.1.35.1

(a) Showing 25 of 4596 features for pDAB105821.1.295.1::pDAB105828.1.35.1

Figure 12C:

```
                              201                                               250
      Ref.Seq. (201) AAAGAGAACTCCTAGATGAATGTCTGCCAGGTAAACAACAGTTGACTT--
             1 (197) AAAGAGAACTCCTAGATGAATGTCTGCCAGGTAAACAACA----------
             2 (196) AAAGAGAACTCCTAGATGAATGTCTGCCAGGTAAACAACAGTTGACTTA-
             3 (196) AAAGAGAACTCCTAGATGAATGTCTGCCAGGTAAACAACAGTTGACTT--
             4 (198) AAAGAGAACTCCTAGATGAATGTCTGCCAGGTAAACAACAGTTGACT---
             5 (196) AAAGAGAACTCCTAGATGAATGTCTGCCAGGTAAACAACAGTTGAC----
             6 (197) AAAGAGAACTCCTAGATGAATGTCTGCCAGGTAAACAACAGCTGACTT--
             7 (186) AAAGAGAACTCCTAGATGAATGTCTGCCAGGTAAACAACAGTTGACTTAG
             8 (197) AAAGAGAACTCCTAGATGAATGTCTGCCAGGTAAACAAC-----------
             9 (194) AAAGAGAACTCCTAGATGAATGTCTGCCAGGTAAACAACAGTTGACTTA-
            10 (195) AAAGAGAACTCCTAGATGAATGTCTGCCAGGTAAACAACAGTTGACTT--
            11 (194) AAAGAGAACTCCTAGATGAATGTCTGCCAGGTAAACAACAGTTGACTTAG
            12 (196) AAAGAGAACTCCTAGATGAATGTCTGCCAGGTAAACAACAGTTGACT---
            13 (197) AAAGAGAACTCCTAGATGAATGTCTGCCAGGTAAACAACAGTTGACTT--
            14 (196) AAAGAGAACTCCTAGATGAATGTCTGCCAGGTAAACAACAGTTGACTTA-
            15 (196) AAAGAGAACTCCTAGATGAATGTCTGCCAGGTAAACAACA----------
            16 (197) AAAGAGAACTCCTAGATGAATGTCTGCCAGGTAAACAA------------
            17 (193) AAAGAGAACTCCTAGATGAATGTCTGCCAGGTAAACAACAGTTGACTTAG
            18 (187) AAAGAGAACTCCTAGATGAATGTCTGCCAGGTAAACAACAGTTGACTTAG
            19 (195) AAAGAGAACTCCTAGATGAATGTCTGCCAGGTAAACAACA----------
            20 (196) AAAGAGAACTCCTAGATGAATGTCTGCCAGGTAAACAACAGTTGAC----
            21 (197) AAAGAGAACTCCTAGATGAATGTCTGCCAGGTAA----------------
            22 (195) AAAGAGAACTCCTAGATGAATGTCTGCCAGGTAAACAACAGTTGACTTA-
            23 (194) AAAGAGAACTCCTAGATGAATGTCTGCCAGGTAAACAACAGTTGACTTAG
            24 (195) AAAGAGAACTCCTAGATGAATGTCTGCCAGGTAAACAACAGTTGA-----
            25 (194) AAAGAGAACTCCTAGATGAATGTCTGCCAGGTAAACAACAGTTG------
```

(b) Showing 25 of 4002 features for pDAB105821.1.309.1::pDAB105828.1.87.1

```
                                    1                                               50
Ref.Seq.(SEQ ID NO:41)(1) CCTTGGGATTTCAGTTGGTAGGTTAAAAATGGGAGTGGCATGGAGAGGAA
       1 (SEQ ID NO:67)(1) CCTTGGGATTTCAGTTGGTAGGTTAAAAATGGGAGTGGCATGGAGAGGAA
       2 (SEQ ID NO:68)(1) CCTTGGGATTTCAGTTGGTAGGTTAAAAATGGGAGTGGCATGGAGAGGAA
       3 (SEQ ID NO:69)(1) CCTTGGGATTTCAGTTGGTAGGTTAAAAATGGGAGTGGCATGGAGAGGAA
       4 (SEQ ID NO:70)(1) CCTTGGGATTTCAGTTGGTAGGTTAAAAATGGGAGTGGCATGGAGAGGAA
       5 (SEQ ID NO:71)(1) CCTTGGGATTTCAGTTGGTAGGTTAAAAATGGGAGTGGCATGGAGAGGAA
       6 (SEQ ID NO:72)(1) CCTTGGGATTTCAGTTGGTAGGTTAAAAATGGGAGTGGCATGGAGAGGAA
       7 (SEQ ID NO:73)(1) CCTTGGGATTTCAGTTGGTAGGTTAAAAATGGGAGTGGCATGGAGAGGAA
       8 (SEQ ID NO:74)(1) CCTTGGGATTTCAGTTGGTAGGTTAAAAATGGGAGTGGCATGGAGAGGAA
       9 (SEQ ID NO:75)(1) CCTTGGGATTTCAGTTGGTAGGTTAAAAATGGGAGTGGCATGGAGAGGAA
      10 (SEQ ID NO:76)(1) CCTTGGGATTTCAGTTGGTAGGTTAAAAATGGGAGTGGCATGGAGAGGAA
      11 (SEQ ID NO:77)(1) CCTTGGGATTTCAGTTGGTAGGTTAAAAATGGGAGTGGCATGGAGAGGAA
      12 (SEQ ID NO:78)(1) CCTTGGGATTTCAGTTGGTAGGTTAAAAATGGGAGTGGCATGGAGAGGAA
      13 (SEQ ID NO:79)(1) CCTTGGGATTTCAGTTGGTAGGTTAAAAATGGGAGTGGCATGGAGAGGAA
      14 (SEQ ID NO:80)(1) CCTTGGGATTTCAGTTGGTAGGTTAAAAATGGGAGTGGCATGGAGAGGAA
      15 (SEQ ID NO:81)(1) CCTTGGGATTTCAGTTGGTAGGTTAAAAATGGGAGTGGCATGGAGAGGAA
      16 (SEQ ID NO:82)(1) CCTTGGGATTTCAGTTGGTAGGTTAAAAATGGGAGTGGCATGGAGAGGAA
      17 (SEQ ID NO:83)(1) CCTTGGGATTTCAGTTGGTAGGTTAAAAATGGGAGTGGCATGGGGAGGAA
      18 (SEQ ID NO:84)(1) CCTTGGGATTTCAGTTGGTAGGTTAAAAATGGGAGTGGCATGGAGAGGAA
      19 (SEQ ID NO:85)(1) CCTTGGGATTTCAGTTGGTAGGTTAAAAATGGGAGTGGCATGGAGAGGAA
      20 (SEQ ID NO:86)(1) CCTTGGGATTTCAGTTGGTAGGTTAAAAATGGGAGTGGCATGGAGAGGAA
      21 (SEQ ID NO:87)(1) CCTTGGGATTTCAGTTGGTAGGTTAAAAATGGGAGTGGCATGGAGAGGAA
      22 (SEQ ID NO:88)(1) CCTTGGGATTTCAGTTGGTAGGTTAAAAATGGGAGTGGCATGGAGAGGAA
      24 (SEQ ID NO:90)(1) CCTTGGGATTTCAGTTGGTAGGTTAAAAATGGGAGTGGCATGGAGAGGAA
      23 (SEQ ID NO:89)(1) CCTTGGGATTTCAGTTGGTAGGTTAAAAATGGGAGTGGCATGGAGAGGAA
      25 (SEQ ID NO:91)(1) CCTTGGGATTTCAGTTGGTAGGTTAAAAATGGGAGTGGCATGGAGAGGAA
```

Figure 12D:

```
                         51                                                  100
         Ref.Seq. (51)   ATAACAGAGGCCCTCCAGCAATAGCTTCTCTGTGATGATAACCCCTATAC
                1 (51)   ATAACAGAGGCCCTCCAGCAATAGCTTCTCTGTGATGATAACCCCTATAC
                2 (51)   ATAACAGAGGCCCTCCAGCAATAGCTTCTCTGTGATGATAACCCCTATAC
                3 (51)   ATAACAGAGGCCCTCCAGCAATAGCTTCTCTGTGATGATAACCCCTATAC
                4 (51)   ATAACAGAGGCCCTCCAGCAATAGCTTCTCTGTGATGATAACCCCTATAC
                5 (51)   ATAACAGAGGCCCTCCAGCAATAGCTTCTCTGTGATGATAACCCCTATAC
                6 (51)   ATAACAGAGGCCCTCCAGCAATAGCTTCTCTGTGATGATAACCCCTATAC
                7 (51)   ATAACAGAGGCCCTCCAGCAATAGCTTCTCTGTGATGATAACCCCTATAC
                8 (51)   ATAACAGAGGCCCTCCAGCAATAGCTTCTCTGTGATGATAACCCCTATAC
                9 (51)   ATAACAGAGGCCCTCCAGCAATAGCTTCTCTGTGATGATAACCCCTATAC
               10 (51)   ATAACAGAGGCCCTCCAGCAATAGCTTCTCTGTGATGATAACCCCTATAC
               11 (51)   ATAACAGAGGCCCTCCAGCAATAGCTTCTCTGTGATGATAACCCCTATAC
               12 (51)   ATAACAGAGGCCCTCCAGCAATAGCTTCTCTGTGATGATAACCCTTATAC
               13 (51)   ATAACAGAGGCCCTCCAGCAATAGCTTCTCTGTGATGATAACCCCTATAC
               14 (51)   ATAACAGAGGCCCTCCAGCAATAGCTTCTCTGTGATGATAACCCCTATAC
               15 (51)   ATAACAGAGGCCCTCCAGCAATAGCTTCTCTGTGATGATAACCCCTATAC
               16 (51)   ATAACAGAGGCCCTCCAGCAATAGCTTCTCTGTGATGATAACCCCTATAC
               17 (51)   ATAACAGAGGCCCTCCAGCAATAGCTTCTCTGTGATGATAACCCCTATAC
               18 (51)   ATAACAGAGGCCCTCCAGCAATAGCTTCTCTGTGATGATAACCCCTATAC
               19 (51)   ATAACAGAGGCCCTCCAGCAATAGCTTCTCTGTGATGATAACCCCTATAC
               20 (51)   ATAACAGAGGCCCTCCAGCAATAGCTTCTCTGTGATGATAACCCCTATAC
               21 (51)   ATAACAGAGGCCCTCCAGCAATAGCTTCTCTGTGATGATAACCCCTATAC
               22 (51)   ATAACAGAGGCCCTCCAGCAATAGCTTCTCTGTGATGATAACCCCTATAC
               24 (51)   ATAACAGAGGCCCTCCAGCAATAGCTTCTCTGTGATGATAACCCCTATAC
               23 (51)   ATAACAGAGGCCCTCCAGCAATAGCTTCTCTGTGATGATAACCCCTATAC
               25 (51)   ATAACAGAGGCCCTCCAGCAATAGCTTCTCTGTGATGATAACCCCTATAC
                         101                                                 150
         Ref.Seq. (101)  TCTATATTTTACAATCCTGTCCCTAGTGAGATGGGCGGGAGTCTTCAATC
                1 (101)  TCTATATTTTACAATCCTGTCCCTAGTGAGATGGGCGGGAGTCTTCAATC
                2 (101)  TCTATATTTTACAATCCTGTCCCTAGTGAGATGGGCGGGAGTCTTCAATC
                3 (101)  TCTATATTTTACAATCCTGTCCCTAGTGAGATGGGCGGGAGTCTTCAATC
                4 (101)  TCTATATTTTACAATCCTGTCCCTAGTGAGATGGGCGGGAGTCTTCAATC
                5 (101)  TCTATATTTTACAATCCTGTCCCTAGTGAGATGGGCGGGAGTCTTCAATC
                6 (101)  TCTATATTTTACAATCCTGTCCCTAGTGAGATGGGCGGGAGTCTTCAATC
                7 (101)  TCTATATTTTACAATCCTGTCCCTAGTGAGATGGGCGGGAGTCTTCAATC
                8 (101)  TCTATATTTTACAATCCTGTCCCTAGTGAGATGGGCGGGAGTCTTCAATC
                9 (101)  TCTATATTTTACAATCCTGTCCCTAGTGAGATGGGCGGGAGTCTTCAATC
               10 (101)  TCTATATTTTACAATCCTGTCCCTAGTGAGATGGGCGGGAGTCTTCAATC
               11 (101)  TCTATATTTTACAATCCTGTCCCTAGTGAGATGGGCGGGAGTCTTCAATC
               12 (101)  TCTATATTTTACAATCCTGTCCCTAGTGAGATGGGCGGGAGTCTTCAATC
               13 (101)  TCTATATTTTACAATCCTGTCCCTAGTGAGATGGGCGGGAGTCTTCAATC
               14 (101)  TCTATATTTTACAATCCTGTCCCTAGTGAGATGGGCGGGAGTCTTCAATC
               15 (101)  TCTATATTTTACAATCCTGTCCCTAGTGAGATGGGCGGGAGTCTTCAATC
               16 (101)  TCTATATTTTACAATCCTGTCCCTAGTGAGATGGGCGGGAGTCTTCAATC
               17 (101)  TCTATATTTTACAATCCTGTCCCTAGTGAGATGGGCGGGAGTCTTCAATC
               18 (101)  TCTATATTTTACAATCCTGTCCCTAGTGAGATGGGCGGGAGTCTTCAATC
               19 (101)  TCTATATTTTACAATCCTGTCCCTAGTGAGATGGGCGGGAGTCTTCAATC
               20 (101)  TCTATATTTTACAATCCTGTCCCTAGTGAGATGGGCGGGAGTCTTCAATC
               21 (101)  TCTATATTTTACAATCCTGTCCCTAGTGAGATGGGCGGGAGTCTTCAATC
               22 (101)  TCTATACTTTACAATCCTGTCCCTAGTGAGATGGGCGGGAGTCTTCAATC
               24 (101)  TCTATATTTTACAATCCTGTCCCTAGTGAGATGGGCGGGAGTCTTCAATC
               23 (101)  TCTATATTTTACAATCCTGTCCCTAGTGAGATGGGCGGGAGTCTTCAATC
               25 (101)  TCTATATTTTACAATCCTGTCCCTAGTGAGATGGGCGGGAGTCTTCAATC
```

Figure 12E:

```
              151        ZFN1                                200
Ref.Seq. (151) CTGTCCCTAGTGGATAAACTGCAAAAGGCGGATCACTGTGGGGTGGCATA
       1 (151) CTGTCCCTAGA---TAAACTGCAAAAGGCGGATCACTGTGGGGTGGCATA
       2 (151) CTGTCCCTAGA---TAAACTGCAAAAGGCGGATCACTGTGGGGTGGCATA
       3 (151) CTGTCCCTAG-----AAACTGCAAAAGGCGGATCACTGTGGGGTGGCATA
       4 (151) CTGTCCCTAG-----AAACTGCAAAAGCGCGATCACTGTCGGGTGGCATA
       5 (151) CTGTCCCTAG-----AAACTGCAAAAGCGCGGATCACTGTCGGGTGGCATA
       6 (151) CTGTCCCT-----------GCAAAAGGCGGATCACTGTGGGGTGGCATA
       7 (151) CTGTCCCTAGT---TAAACTGCAAAAGGCGGATCACTGTGGGGTGGCATA
       8 (151) CTGTCCCTAG-----AAACTGCAAAAGGCGGATCACTGTGGGGTGGCATA
       9 (151) CTGTCCCTAGA---TAAACTGCAAAAGGCGGATCACTGTGGGGTGGCATA
      10 (151) CTGTCCCTAG-----AAACTGCAAAAGGCGGATCACTGTGGGGTGGCATA
      11 (151) CTGTCCCTAG-----AAACTGCAAAAGGCGGATCACTGTGGGGTGGCATA
      12 (151) CTGTCCCTAGA---TAAACTGCAAAAGGCGGATCACTGTGGGGTGGCATA
      13 (151) CTGTCCCTAGA---TAAACTGCAAAAGGCGGATCACTGTGGGGTGGCCTA
      14 (151) CTGTCCCTAGA---TAAACTGCAAAAGGCGGATCACTGTGGGGTGGCATA
      15 (151) CTGTCCCTAGA---TAAACTGCAAAAGGCGGATCACTGTGGGGTGGCATA
      16 (151) CTGTCCCTAG-----AAACTGCAAAACGCGGATCACTGTGGGGTGGCATA
      17 (151) CTGTCCCTAGT---TAAACTGCAAAAGGCGGATCACTGTGGGGTGGCATA
      18 (151) CTGTCCCTAGT---TAAACTGCAAAAGGCGGATCACTGTGGGGTGGCATA
      19 (151) CTGTCCCTAGT---TAAACTGCAAAAGGCGGATCACTGTGGGGTGGCATA
      20 (151) CTGTCCCTAG----TAAACTGCAAAAGGCGGATCACTGTGGGGTGGCATA
      21 (151) CTGTCCCTAG-----AAACTGCAAAAGGCGGATCACTGTGGGGTGGCATA
      22 (151) CTGTCCCTAGA---TAAACTGCAAAAGGCGGATCACTGTGGGGTGGCATA
      24 (151) CTGTCCCTAGT---TAAACTGCAAAAGGCGGATCACTGTGGGGTGGCATA
      23 (151) CTGTCCCTAGT---TAAACTGCAAAAGGCGGATCACTGTGGGGTGGCATA
      25 (151) CTGTCCCTAGT---TAAACTGCAAAAGGCGGATCACTGTGGGGTGGCATA
              201                                            250
Ref.Seq. (201) AAAGAGAACTCCTAGATGAATGTCTGCCAGGTAAACAACAGTTGACTT--
       1 (198) AAAGAGAACTCCTAGATGAATGTCTGCCAGGTACACAACAGTTGAC----
       2 (198) AAAGAGAACTCCTAGATGAATGTCTGCCAGGTAAACAACA----------
       3 (196) AAAGAGAACTCCTAGATGAATGTCTGCCAGGTAAACAACAGCTGAC----
       4 (196) AAAGAGAACTCCTAGATGAATGTCTGCCAGGTAAACAACA----------
       5 (196) AAAGAGAACTCCTAGATGAATGTCTGCC----------------------
       6 (189) AAAGAGAACTCCTAGATGAATGTCTGCCAGGTAAACAACAGTTGACTTAG
       7 (198) AAAGAGAAATCCTAGATGAATGTCT-------------------------
       8 (196) AAAGAGAACTCCTAGATGAATGTCTTCCAGGTAAACAACA----------
       9 (198) AAAGAGAACTCCTAGATGAATGTCTGCCAGGTAAACAACAGTTGAC----
      10 (196) AAAGAGAACTCCTAGATGAATGACTGCCAGGTAAACAACAGTTGACT---
      11 (196) AAAGAGAACTCCTAGATGAATGTCTGCCAGGTAAACAACAGTTGACTTA-
      12 (198) AAAGAGAACTCCTAGATGAATGTCTGCCAGGTAAACAACAGTTGAC----
      13 (198) AAAGAGAACTCCTAGATGAATGTCTGCCAGGTAAACAACAGTTGAC----
      14 (198) AAAGAGAACTCCTAGATGAATGTCTGCCAGGTAAACAAC-----------
      15 (198) AAAGAGAACTCCTAGATGAATGTCTGCCAGGTAAACAACAG---------
      16 (196) AAAGAGAACTCCTAGATGAATGTCTGCCAGGTAAACAACAGT--------
      17 (198) AAAGAGAACTCCTAGATGAATGTCTGCCAGGTAAACAACA----------
      18 (198) AAAGAGAACTCCTAGATGAATGTCTGCCAGGTAAACAACA----------
      19 (198) AAAGAGAAATCCAGATGAATGTCTGCCAGGTAAACAACA-----------
      20 (197) AAAGAGAACTCCTAGATGAATGTCTGCCA---------------------
      21 (196) AAAGAGAACTCCTAGATGAATGTCTGCCAGGTAAACAACAGTTGACTT--
      22 (198) AAAGAGAACTCCTAGATGAATGTCTGCCAGGTAAACAACAGTTGACT---
      24 (198) AAAGAGAACTCCTAGATGAATGTCTGCCAGGTAAACAACAG---------
      23 (198) AAAGAGAACTCCTAGATGAATGTCTGCCAGGTAAACAACAGTTGACT---
      25 (198) AAAGAGAACTCCTAGATGAATGTCTGCCA---------------------
```

DNA DETECTION METHODS FOR SITE SPECIFIC NUCLEASE ACTIVITY

CROSS-REFERENCE TO RELATED APPLICATIONS

This application claims priority to U.S. Provisional Patent Application No. 61/736,856, filed Dec. 13, 2012. The contents of the entirety of each of the foregoing are hereby incorporated in their entireties herein by this reference.

REFERENCE TO SEQUENCE LISTING SUBMITTED ELECTRONICALLY

The official copy of the sequence listing is submitted electronically via EFS-Web as an ASCII formatted sequence listing with a file named "DNA DETECTION METHOD", created on Nov. 26, 2012, and having a size of 3,640 bytes and is filed concurrently with the specification. The sequence listing contained in this ASCII formatted document is part of the specification and is herein incorporated by reference in its entirety.

FIELD OF THE INVENTION

The present disclosure relates in part to a method for screening genomic loci of plant events. More particularly, the present disclosure relates in part to a high throughput method for detecting and identifying plant events that contain a disruption within a targeted genomic loci. In addition, the present disclosure relates in part to a high throughput method for detecting and identifying plant events that contain an exogenous donor DNA polynucleotide inserted within a targeted genomic loci. The method is readily applicable for screening plant events produced via a targeting method which results from the use of a site specific nuclease.

BACKGROUND OF THE INVENTION

Targeted genome modification of plants has been a long-standing and elusive goal of both applied and basic research. Methods and compositions to target and cleave genomic DNA by site specific nucleases (Zinc Finger Nucleases (ZFNs), Meganucleases, CRISPRS and TALENS) are being developed to reach this goal. The site specific cleavage of genomic loci by ZFNs can be used, for example, to induce targeted mutagenesis, induce targeted deletions of cellular DNA sequences, and facilitate targeted recombination of an exogenous donor DNA polynucleotide within a predetermined genomic locus. See, for example, U.S. Patent Publication No. 20030232410; 20050208489; 20050026157; 20050064474; and 20060188987, and International Patent Publication No. WO 2007/014275, the disclosures of which are incorporated by reference in their entireties for all purposes. U.S. Patent Publication No. 20080182332 describes use of non-canonical zinc finger nucleases (ZFNs) for targeted modification of plant genomes and U.S. Patent Publication No. 20090205083 describes ZFN-mediated targeted modification of a plant EPSPs genomic locus. In addition, Moehle et al. (2007) Proc. Natl. Acad. Sci. USA 104(9): 3055-3060 describe using designed ZFNs for targeted gene addition at a specified genomic locus. Current methods of targeting typically involve co-transformation of plant tissue with a donor DNA polynucleotide containing at least one transgene and a site specific nuclease (e.g., ZFN) which is designed to bind and cleave a specific genomic locus. The donor DNA polynucleotide is stably inserted within the cleaved genomic locus resulting in targeted gene addition at a specified genomic locus.

Unfortunately, reported and observed frequencies of targeted genomic modification indicate that targeting a genomic loci within plants is relatively inefficient. The reported inefficiency necessitates the screening of a large number of plant events to identify a specific event containing the targeted genomic loci. Most current reported plant event analyses rely on a single analytical method for confirming targeting, which may lead to inaccurate estimation of targeting frequencies and low confidence outcomes.

Therefore, there is a need in the art for screening methods, optionally applicable as high throughput methods, for the rapid identification of plant events containing a targeted genomic loci. In addition, as targeted gene insertion occurs in conjunction with random gene insertion, desirable screening methods would specifically identify targeting of genomic loci within a background of random insertions.

BRIEF SUMMARY OF THE INVENTION

In an embodiment, the disclosure relates to a method for identifying the presence of a donor DNA polynucleotide inserted within a targeted genomic locus comprising amplifying in a first amplification reaction a genomic DNA sample comprising the targeted genomic locus using a first plurality of oligonucleotides that bind under hybridization conditions proximal to the targeted genomic locus to thereby generate a first amplicon comprising the targeted genomic locus, and detecting the presence or absence of the first amplicon, wherein the absence of the first amplicon indicates the presence of the donor DNA polynucleotide within the targeted genomic locus.

In a further embodiment, the method comprises amplifying in a second amplification reaction the genomic DNA sample using a second plurality of oligonucleotides that bind under hybridization conditions proximal to the targeted genomic locus and within the donor DNA polynucleotide to generate a second amplicon comprising at least a portion of the targeted genomic locus and at least a portion of the donor DNA polynucleotide, and detecting the presence or absence of the second amplicon, wherein the presence of an amplified product indicates the presence of the donor DNA polynucleotide within the targeted genomic locus.

In yet another embodiment, the method comprises identification of a disruption of a genomic locus from a plurality of plant cells comprising amplifying in a first amplification reaction a genomic DNA sample comprising the disrupted genomic locus using a plurality of oligonucleotides that bind under hybridization conditions proximal to the disrupted genomic locus to generate a first amplicon comprising the disrupted genomic locus, quantitating the results of the first amplification reaction, amplifying in a second amplification reaction a genomic DNA sample comprising the disrupted genomic locus using the plurality of oligonucleotides that bind under hybridization conditions proximal to the disrupted genomic locus, to thereby generate a second amplicon comprising the disrupted genomic locus, quantitating the results of the second amplification reaction, and comparing the quantity of the first and second amplification reactions, wherein the quantity of the first amplification reaction comprises a lower quantity of amplified product as compared to the second amplification reaction thereby indicating the disruption of a genomic locus in the first amplicon samples.

In another embodiment, the disclosure describes a method for identifying a disruption of a genomic locus comprising amplifying in a first amplification reaction a genomic DNA sample comprising the disrupted genomic locus using a plurality of oligonucleotides that bind under hybridization conditions proximal to the disrupted genomic locus to generate a first amplicon comprising the disrupted genomic locus, and detecting the presence or absence of the first amplicon, wherein the absence of the amplicon indicates the disruption of a genomic locus.

Further embodiments of the method include quantitating the results of the first amplification reaction, quantitating the results of the second amplification reaction, comparing the results of the first and second amplification reactions, and determining the presence or absence of the donor DNA polynucleotide within the targeted genomic locus, wherein the donor DNA polynucleotide is confirmed as inserted within the targeted genomic locus if the first amplicon is absent and the second amplicon is present.

As an embodiment, the first or second amplification reactions are run in a single tube or well in a multiplex format.

In another aspect, an embodiment of the disclosure includes quantitating the results of the first and second amplification reactions comprising producing a signature profile for one or both of the first and second amplification reactions. In an exemplary aspect of the embodiment, the signature profile may be selected from the group consisting of a melting temperature curve signature profile and a fluorescence signature profile.

Additional embodiments include a signature profile produced from an intercalating DNA dye or a fluorescent dye. Wherein, the intercalating dye comprises a cyanine dye such as a SYTO13® dye. As an embodiment, the SYTO13® dye is used in an amplification reaction at a concentration of less than 10 µM, less than 4 µM, or less than 2.7 µM. In additional embodiments the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye. In an embodiment the first or second plurality of oligonucleotides, or both, comprise a fluorescent dye.

In embodiments, the present disclosure relates to methods and compositions for identifying the presence of a donor insertion within a targeted genomic locus, and selecting a transgenic event comprising a donor insertion within a targeted genomic locus. An additional embodiment includes the plant, comprising the transgenic event.

Further embodiments may comprise a dicot plant, wherein the dicot plant is selected from the group consisting of a soybean plant, a canola plant and a cotton plant. In addition, further embodiments may comprise a monocot plant, wherein the monocot plant is selected from the group consisting of a corn plant, a rice plant, and wheat plant.

Additional embodiments include a genomic locus that is cleaved by a site specific nuclease. Exemplary site specific nucleases may comprises a Zinc Finger Nuclease, a Meganuclease, CRISPR, or a TALEN nuclease or any other site specific nuclease.

In another aspect, embodiments of the disclosure include an amplification reaction, wherein amplify is completed using a polymerase chain reaction.

Further embodiments of the disclosure include an amplicon comprising a 5' junction and a 3' junction of the donor DNA polynucleotide and the targeted genomic locus. In addition, embodiments of the disclosure include an amplicon comprising a 5' junction or a 3' junction of the donor DNA polynucleotide and the targeted genomic locus.

Embodiments also include a donor DNA polynucleotide comprising at least one gene expression cassette.

In addition to the exemplary aspects and embodiments described above, further aspects and embodiments will become apparent by study of the following descriptions.

BRIEF DESCRIPTION OF THE FIGURES

FIG. 3A depicts a targeted genomic locus ("Locus") with no transgene insertion. In-Out PCR will result in no amplified product. FIG. 3B depicts the Locus with targeted transgene insertion. In-Out PCR will result in a 2 kb amplicon from the 5' end of the locus and a 1.5 kb amplicon from the 3' end.

FIG. 4A depicts a fluorescence signal signature profile generated from amplification reactions using SYTO13® dye (Invitrogen, Carlsbad, Calif.), which can be used to identify positive transgene insertion events. FIG. 4B depicts melting temperature signature profiles generated from amplification reactions of samples as compared to a positive control, which can be used to confirm the positive fluorescence signals.

FIG. 5 shows targeted events that were identified using the disruption assay and the In-Out PCR reaction of the presently disclosed subject matter.

FIG. 8 (a) provides an illustration of the genomic fragment containing the ELP which was produced by the integration of a T-strand from pDAB105818. This schematic identifies the relative location of primers and probes (MAS621, MAS622 and probe UPL67) used for the disruption assay. FIG. 8 (b) provides the screening results of 354 pat positive events. A disrupted ELP locus is indicated by drop in detectable qPCR signal. Accordingly samples shown in the top bracket do not contain a disrupted ELP genomic locus and samples shown in the bottom bracket do contain a disrupted ELP genomic locus.

FIG. 9A depicts a melting temperature signal profile generated from amplification reactions of the 5' donor/ELP locus junction using SYTO13® dye (Invitrogen, Carlsbad, Calif.), which can be used to identify positive transgene insertion events. FIG. 9B depicts a melting temperature signal profile generated from amplification reactions of the 3' donor/ELP locus junction using SYTO13® dye (Invitrogen, Carlsbad, Calif.), which can be used to identify positive transgene insertion events.

FIG. 11 (a) shows the disruption assay results of 1125 samples crossed with eZFN1 excisors: 425 with ELP copy number less than 0.05 (cut), 95 between 0.05 to 0.4 (chimeric). FIG. 11 (b) shows the disruption assay results of 697 samples crossed with eZFN8 excisors: 488 with ELP copy number less than 0.05, 1 between 0.05 to 0.4.

DETAILED DESCRIPTION

Figure 1:
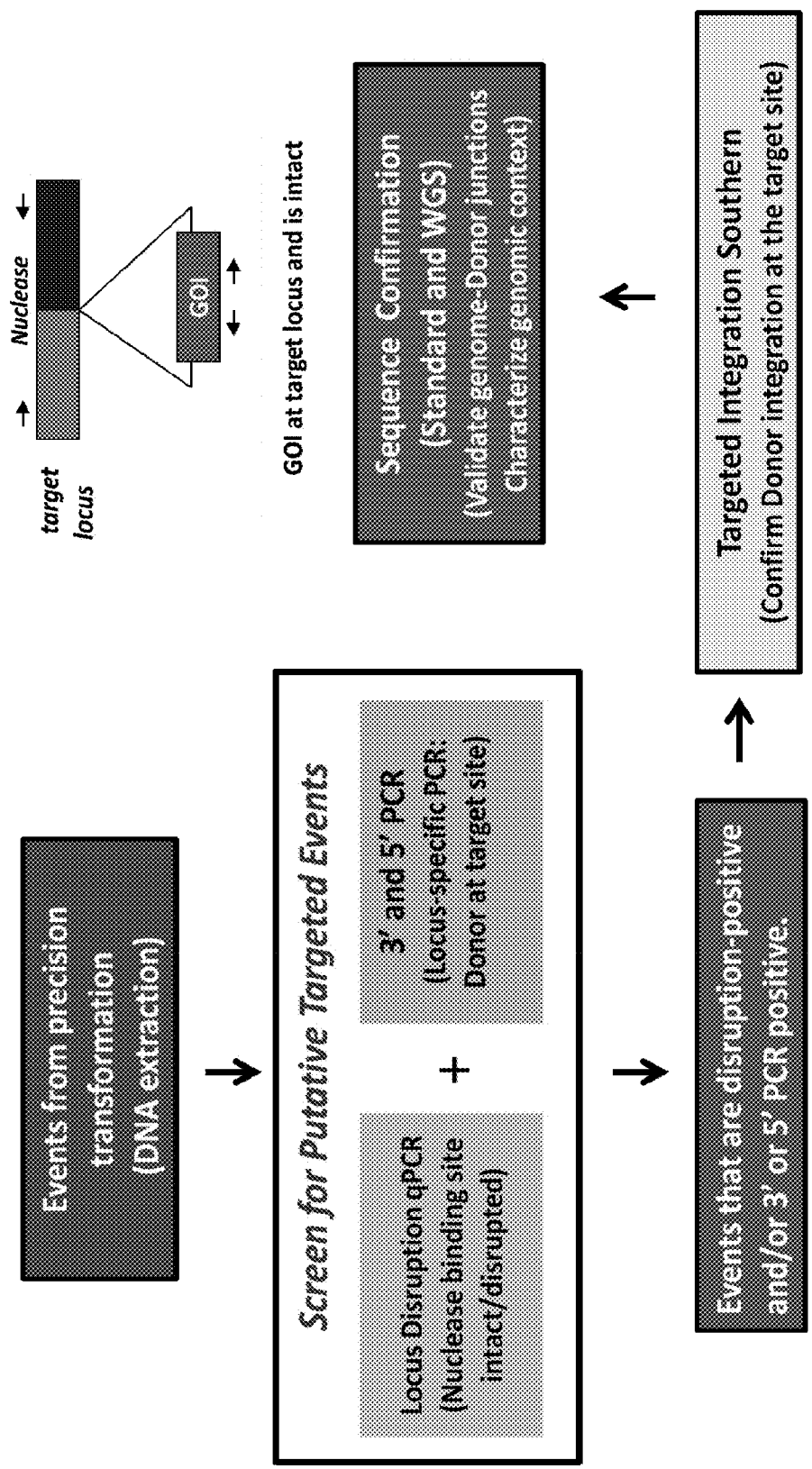
FIG. 1 illustrates an analytical process for identifying plant events comprising a targeted genomic locus.

Novel methods have now been invented for rapid screening, identification and characterization of site specific nuclease targeted plant events. The methods can be used to analyze the intactness of the genomic target locus via a first amplification reaction to determine if the genomic target locus has been disrupted. Events which are identified to contain a disrupted genomic locus can be subsequently screened via a second amplification reaction to confirm the presence of an exogenous donor DNA polynucleotide within the targeted genomic locus. As such, large numbers of plant events can be analyzed and screened to identify and select specific events which have a donor DNA polynucleotide inserted within a targeted genomic locus. The presently disclosed subject matter further includes plants and plant cells comprising nuclease targeted plant events selected utilizing the novel screening methods.

Demonstrated herein are novel methods for screening plant events for the disruption of a genomic locus, which is a result of genomic DNA cleavage by a site specific nuclease. The disrupted genomic locus may comprise the presence of a donor DNA polynucleotide, or the disrupted genomic locus may comprise insertions and/or deletions (also described as InDels). The methods utilize two initial amplification reactions as a screening assay. The first amplification reaction is a disruption assay, wherein the presence of a donor DNA polynucleotide inserted within a targeted genomic locus is identified by an amplification reaction in which the absence of an amplicon indicates that a donor DNA polynucleotide is present within the targeted genomic locus. The second amplification reaction is an "In-Out" PCR amplification reaction for screening the 3' and/or the 5' junction sequences of a donor DNA polynucleotide targeted genomic locus. The presence of an amplified product which contains the 3' and/or 5' junction sequence indicates that the donor DNA polynucleotide is present within the targeted genomic locus.

By deploying two distinct amplification reaction screening assays, the disruption amplification reaction and the In-Out amplification reaction, the probability of identifying a positive target event from the large number of non-targeted events is greatly increased. The disruption amplification reaction was designed to allow for rapid analysis of a large number of samples in a high throughput manner. Furthermore, this assay can identify and characterize events for both donor DNA polynucleotide insertion or ZFN cleavage within a targeted genomic locus. The In-Out amplification reaction provides an alternative analytical approach. This assay is used to identify the presence of the 3' and 5' junctions to confirm the presence of a donor DNA polynucleotide inserted within a targeted genomic locus. The In-Out amplification reaction can be used to confirm that the targeted events identified in the disruption assay actually contain a complete, full-length targeted insertion within a genomic locus. When the disruption amplification reaction is run in conjunction with the In-Out amplification reaction, the compiled data can be analyzed to determine the limiting factors for targeting of a donor DNA polynucleotide within a genomic locus (e.g., ZFN cleavage or donor insertion as a limiting factor for producing events containing a donor DNA polynucleotide within a targeted genomic locus). Utilizing two different screening assays with varying methodology increases the likelihood of finding a targeted event which contains a donor DNA polynucleotide within a targeted genomic locus. Moreover, the disclosed methods can be deployed as high throughput assays allowing for the rapid and efficient identification of a subset of samples that can then be further analyzed by other molecular confirmation methods. The disclosed screening assays describe high quality, high throughput processes for identifying and obtaining targeted transgene insertion events. Furthermore, the methodology is readily applicable for the analysis of any plant species.

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms ""comprises"," ""comprising"," ""includes"," ""including"," ""has"," ""having"," ""contains"," or ""containing"," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, ""or"" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles ""a"" and ""an"" preceding an element or component of an embodiment of the disclosure are intended to be nonrestrictive regarding the number of instances, i.e., occurrences of the element or component. Therefore ""a"" or ""an"" should be read to include one or at least one, and the singular word form of the element or component also includes the plural unless the number is obviously meant to be singular.

The term ""invention"" or ""present invention"" as used herein is a non-limiting term and is not intended to refer to any single embodiment of the particular invention but encompasses all possible embodiments as disclosed in the application.

The term "plant" as used herein includes, but is not limited to, any descendant, cell, tissue, or part of a plant.

Described herein are methods of identifying the presence of a donor DNA polynucleotide inserted within a targeted genomic loci. DNA polynucleotides for insertion can also be referred to, and are intended to include, as "exogenous" polynucleotides, "donor" polynucleotides or "molecules" or "transgenes."

In certain embodiments, the donor DNA polynucleotide includes sequences (e.g., coding sequences, also referred to as transgenes) greater than 1 kb in length, for example between 2 and 200 kb, between 2 and 10 kb (or any value therebetween). The donor DNA polynucleotide can also include at least one site specific nuclease target site, for example at least one ZFN, Meganuclease, CRISPR, or TALEN target site may be included in the donor DNA polynucleotide. The donor DNA polynucleotide can include at least 1 target site, for example for a pair of ZFNs, CRISPRs, or TALENs to recognize and bind and cleave. Typically, the nuclease target sites are outside the transgene sequences, for example, 5' or 3' to the transgene sequences, for cleavage and removal of the intervening transgene, if desired. The nuclease cleavage site(s) may be for any nuclease(s). In certain embodiments, the nuclease target site(s) contained in the double-stranded donor DNA polynucleotide are for the same nuclease(s) used to cleave the endogenous genomic target into which the donor DNA polynucleotide is inserted.

The transgenes comprised within the donor DNA polynucleotide sequences described herein may be isolated from plasmids, cells or other sources using standard techniques known in the art such as PCR. Donor DNA polynucleotide sequences for use can include varying types of topology, including circular supercoiled, circular relaxed, linear and the like. Alternatively, they may be chemically synthesized using standard oligonucleotide synthesis techniques. In addition, donor DNA polynucleotide sequences may be methylated or lack methylation. Donor DNA polynucleotide sequences may be in the form of bacterial or yeast artificial chromosomes (BACs or YACs), or as plasmid vectors. Donor DNA polynucleotide sequences may be from a T-strand which is introduced into a plant cell by *Agrobacterium tumefaciens*.

The double-stranded donor DNA polynucleotides described herein may include one or more non-natural bases and/or backbones. In particular, insertion of a donor DNA polynucleotide sequence with methylated cytosines may be carried out using the methods described herein to achieve a state of transcriptional quiescence in a region of interest.

The donor DNA polynucleotide may comprise any exogenous sequence of interest. Exemplary donor DNA polynucleotide sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate herbicide resistance (e.g., HPPD resistance, 2,4-D resistance, glufosinate resistance, or glyphosate resistance, in addition to other know herbicide resistance proteins), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, HIS, MYC, TAP, HA or any detectable amino acid sequence.

The terms "polynucleotide," "nucleic acid," and "nucleic acid molecule" are intended to encompass a singular nucleic acid as well as plural nucleic acids, a nucleic acid fragment, variant, or derivative thereof, or construct, e.g., messenger RNA (mRNA) or plasmid DNA (pDNA). A polynucleotide or nucleic acid can contain the nucleotide sequence of the full-length cDNA sequence, or a fragment thereof, including the untranslated 5' and 3' sequences and the coding sequences. Unless specified otherwise, a polynucleotide or nucleic acid can be composed of any polyribonucleotide or polydeoxyribonucleotide, which may be unmodified RNA or DNA or modified RNA or DNA. For example, a polynucleotide or nucleic acid can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. These terms also embrace chemically, enzymatically, or metabolically modified forms of a polynucleotide or nucleic acid.

A polynucleotide or nucleic acid sequence can be referred to as "isolated," in which it has been removed from its native environment. For example, a heterologous polynucleotide or nucleic acid encoding a polypeptide or polypeptide fragment having glyphosate tolerance activity contained in a vector is considered isolated for the purposes of the present disclosure. Further examples of an isolated polynucleotide or nucleic acid include recombinant polynucleotide maintained in heterologous host cells or a purified (partially or substantially) polynucleotide or nucleic acid in solution. An isolated polynucleotide or nucleic acid according to embodiments of the present disclosure further includes such molecules produced synthetically. An isolated polynucleotide or nucleic acid in the form of a polymer of DNA may be comprised of one or more segments of cDNA, genomic DNA or synthetic DNA.

The term "gene" refers to a nucleic acid sequence encodes functional product molecules, either RNA or protein, optionally including regulatory sequences preceding (5' non-coding sequences) and following (3' non-coding sequences) the coding sequence.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, translation leader sequences, introns, polyadenylation recognition sequences, RNA processing site, effector binding site and stem-loop structure.

As used herein, the term "polypeptide" is intended to encompass a singular "polypeptide" as well as plural "polypeptides" and fragments thereof, and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. Thus, reference to "isolated" signifies the involvement of the "hand of man" as described herein. For example, an isolated polypeptide can be removed from its native or natural environment. Recombinant polypeptides and proteins expressed in host cells are considered isolated for purposes of the disclosure, as are native or recombinant polypeptides which have been separated, fractionated, or partially or substantially purified by any suitable technique.

As used herein, "native" refers to the form of a polynucleotide, gene or polypeptide as found in nature with its own regulatory sequences, if present.

As used herein, "endogenous" refers to the native form of a polynucleotide, gene or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism.

As used herein, "heterologous" refers to a polynucleotide, gene or polypeptide not normally found in the host organism but that is introduced into the host organism. "Heterologous polynucleotide" includes a native coding region, or portion thereof, that is reintroduced into the source organism in a form that is different from the corresponding native polynucleotide. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide. The subject genes and proteins can be fused to other genes and proteins to produce chimeric or fusion proteins. The genes and proteins useful in accordance with embodiments of the subject disclosure include not only the specifically exemplified full-length sequences, but also portions, segments and/or fragments (including contiguous fragments and internal and/or terminal deletions compared to the full-length molecules) of these sequences, variants, mutants, chimerics, and fusions thereof.

In an embodiment, the donor DNA polynucleotide comprises a polynucleotide encoding any polypeptide of which expression in the cell is desired, including, but not limited to a gene expression cassette comprising promoters, 3' UTR's, herbicide resistance traits, insect resistance traits, modified oil traits, agronomic traits, and functional fragments of any of the above. The coding sequences may be, for example, cDNAs.

The term "promoter" refers to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (e.g., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of embodiments of the disclosure. Expression may also refer to translation of mRNA into a polypeptide.

The term "overexpression" as used herein, refers to expression that is higher than endogenous expression of the same or related gene. A heterologous gene is overexpressed if its expression is higher than that of a comparable endogenous gene.

As used herein the term "transformation" refers to the transfer and integration of a nucleic acid or fragment into a host organism, resulting in genetically stable inheritance. Host organisms containing the transformed nucleic acid fragments are referred to as "transgenic" or "recombinant" or "transformed" organisms. Known methods of transformation include *Agrobacterium tumefaciens*- or *Agrobacterium rhizogenes*-mediated transformation, calcium phosphate transformation, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or PEG transformation as well as other possible methods.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

The term "percent identity" (or "% identity"), as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. See Russell, R., and Barton, G., "Structural Features can be Unconserved in Proteins with Similar Folds," J. Mol. Biol. 244, 332-350 (1994), at p. 337, which is incorporated herein by reference in its entirety.

In addition, methods to determine identity and similarity are codified in publicly available computer programs. Sequence alignments and percent identity calculations can be performed, for example, using the AlignX program of the VECTOR NTI® suite (Invitrogen, Carlsbad, Calif.) or MEGALIGN™ program of the LASERGENE™ bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, *CABIOS.* 5:151-153 (1989); Higgins, D. G. et al., *Comput. Appl. Biosci.,* 8:189-191 (1992)) and found in the MEGALIGN™ program of the LASERGENE™ bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MEGALIGN™ v6.1 program of the LASERGENE™ bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

The nucleic acid probes and primers of embodiments of the present disclosure can hybridize under hybridization conditions to a target DNA sequence within an amplification reaction. Any conventional nucleic acid hybridization or amplification method can be used to identify the presence of donor DNA polynucleotide inserted within a targeted genomic locus. Nucleic acid molecules, oligonucleotides or fragments thereof are capable of specifically hybridizing to other nucleic acid molecules under certain conditions. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if the two nucleic acid molecules exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe, it need only exhibit the minimal complementarity of sequence to be able to form a stable double-stranded structure under the particular solvent and salt concentrations employed.

Factors that affect the stringency of hybridization are well-known to those of skill in the art and include, but are not limited to, temperature, pH, ionic strength, and concentration of organic solvents such as, for example, formamide and dimethyl sulfoxide. As is known to those of skill in the art, hybridization stringency is increased by higher temperatures, lower ionic strength and lower solvent concentrations.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1.0 M NaCl, 0.1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 0.1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

Specificity is typically a function of post-hybridization washes, the critical factors being the ionic strength and temperature of the final wash solution. For DNA-DNA hybrids, the $T_m$ can be approximated from the equation $T_m=81.5°$ C.$+16.6$ (log M)$+0.41$(% GC)$-0.61$(% form.)$-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al., *Short Protocols in Molecular Biology*, pages 2-40, 3$^{rd}$ Ed. (1997) and Sambrook et al. (1989).

In an embodiment, the subject disclosure relates to the introduction of a donor DNA polynucleotide which is inserted within a targeted genome locus. Standard recombinant DNA and molecular cloning techniques for the construction of a donor DNA polynucleotide that as an embodiment comprises a gene expression cassette as used here are well known in the art and are described, e.g., by Sambrook et al., *Molecular Cloning: A Laboratory Manual*, Second Edition, Cold Spring Harbor Laboratory Press, Cold Spring Harbor, N.Y. (1989); and by Silhavy et al., *Experiments with Gene Fusions*, Cold Spring Harbor Laboratory Press, Cold Spring Harbor, N.Y. (1984); and by Ausubel et al., *Current Protocols in Molecular Biology*, published by Greene Publishing Assoc. and Wiley-Interscience (1987).

In methods disclosed herein, a number of promoters that direct expression of a gene in a plant can be employed. Such promoters can be selected from constitutive, chemically-regulated, inducible, tissue-specific, and seed-preferred promoters. The promoter used to direct expression of a nucleic acid depends on the particular application. For example, a strong constitutive promoter suited to the host cell is typically used for expression and purification of expressed proteins.

Non-limiting examples of preferred plant promoters include promoter sequences derived from *A. thaliana* ubiquitin-10 (ubi-10) (Callis, et al., 1990, *J. Biol. Chem.*, 265: 12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139). Other constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

Other applicable plant promoters include tissue specific and inducible promoters. An inducible promoter is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in embodiments of the instant disclosure. See Ward et al., Plant Mol. Biol. 22: 361-366 (1993). Exemplary inducible promoters include ecdysone receptor promoters (U.S. Pat. No. 6,504,082); promoters from the ACE1 system which respond to copper (Mett et al., Proc. Natl. Acad. Sci. 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); or promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-la promoter, which is activated by salicylic acid (see Ono S, Kusama M, Ogura R, Hiratsuka K., "Evaluation of the Use of the Tobacco PR-la Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al., (1997) Plant J. 12(2): 255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as PSCS (Zang et al., (1997) Plant Sciences 129:81-89); cold-inducible promoters, such as, cor15a (Hajela et al., (1990) Plant Physiol. 93:1246-1252), cor15b (Wilhelm et al., (1993) Plant Mol Biol 23:1073-1077), wsc1 (Ouellet et al., (1998) FEBS Lett. 423-324-328), ci7 (Kirch et al., (1997) Plant Mol Biol. 33:897-909), ci21A (Schneider et al., (1997) Plant Physiol. 113:335-45); drought-inducible promoters, such as Trg-31 (Chaudhary et al., (1996) Plant Mol. Biol. 30:1247-57), rd29 (Kasuga et al., (1999) Nature Biotechnology 18:287-291); osmotic inducible promoters, such as Rab17 (Vilardell et al., (1991) Plant Mol. Biol. 17:985-93) and osmotin (Raghothama et al., (1993) Plant Mol Biol 23:1117-28); and heat inducible promoters, such as heat shock proteins (Banos et al., (1992) Plant Mol. 19:665-75; Marrs et al., (1993) Dev. Genet. 14:27-41), smHSP (Waters et al., (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al., (1993) Mol. Gen. Genetics 236:331-340). Certain promoters are inducible by wounding, including the Agrobacterium pMAS promoter (Guevara-Garcia et al., (1993) Plant J. 4(3):495-505) and the Agrobacterium ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al., (1989) The Plant Cell Vol. 1, 839-853), and the maize globulin-1 gene (Belanger, et al. (1991) Genetics 129:863-972). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al., (1994) T-DNA tagging of a seed coat-specific cryptic promoter in tobacco. Plant J. 4: 567-577), the P-gene promoter from corn (Chopra et al., (1996) Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from corn (Belenger and Kriz (1991) Molecular basis for Allelic Polymorphism of the maize Globulin-1 gene. Genetics 129: 863-972), and promoters that direct expression to the seed coat or hull of corn kernels, for example the pericarp-specific glutamine synthetase promoter (Muhitch et al., (2002) Isolation of a Promoter Sequence From the Glutamine Synthetase$_{1-2}$ Gene Capable of Conferring Tissue-Specific Gene Expression in Transgenic Maize. Plant Science 163:865-872).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the protein, and signals required, e.g., for efficient polyadenylation of the transcript, transcriptional termination, ribosome binding sites, or translation termination. Additional elements of the cassette may include, e.g., enhancers and heterologous splicing signals.

Other components of the vector may be included, also depending upon intended use of the gene. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) Plant Mol. Biol., 34: 687-692 and International Patent Publication No. WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846 (nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al., Nucleic Acids Res. 17:7891-7903 (1989); Joshi et al. Nucleic Acid Res. 15:9627-9639 (1987).

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al., Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al., Nature 353:90-94 (1991); untranslated leader from the coat protein mRNA of alfalfa mosaic virus (AMV RNA 4), Jobling et al., Nature 325:622-625 (1987); Tobacco mosaic virus leader (TMV), Gallie et al., (1989) Molecular Biology of RNA, pages 237-256; and maize chlorotic mottle virus leader (MCMV) Lommel et al., Virology 81:382-385 (1991). See also Della-Cioppa et al., Plant Physiology 84:965-968 (1987).

The construct can also contain sequences that enhance translation and/or mRNA stability such as introns. An example of one such intron is the first intron of gene II of the histone H3.III variant of *Arabidopsis thaliana*. Chaubet et al., Journal of Molecular Biology, 225:569-574 (1992).

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (U.S. Pat. No. 5,510,417), *Zea mays* Brittle-1 chloroplast transit peptide (Nelson et al., Plant Physiol 117(4):1235-1252 (1998); Sullivan et al., Plant Cell 3(12):1337-48; Sullivan et al., Planta (1995) 196(3): 477-84; Sullivan et al., J. Biol. Chem. (1992) 267(26): 18999-9004) and the like. In addition, chimeric chloroplast transit peptides are known in the art, such as the Optimized Transit Peptide (U.S. Pat. No. 5,510,471). Additional chloroplast transit peptides have been described previously in U.S. Pat. No. 5,717,084 and U.S. Pat. No. 5,728,925. One skilled in the art will readily appreciate the many options available in expressing a product to a particular organelle. For example, the barley alpha amylase sequence is often used to direct expression to the endoplasmic reticulum (Rogers, J. Biol. Chem. 260:3731-3738 (1985)).

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants can be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, (1983); Meijer et al., Plant Mol. Biol. 16:807-820, (1991)); neomycin phosphotransferase, which confers resistance to the aminoglycosides neomycin, kanamycin and paromycin (Herrera-Estrella, EMBO J. 2:987-995, 1983 and Fraley et al., Proc. Natl. Acad. Sci USA 80:4803 (1983)) and hygromycin phosphotransferase, which confers resistance to hygromycin (Marsh, Gene 32:481-485, (1984); see also Waldron et al., Plant Mol. Biol. 5:103-108, (1985); Zhijian et al., Plant Science 108:219-227, (1995)); trpB, which allows cells to utilize indole in place of tryptophan; hisD, which allows cells to utilize histinol in place of histidine (Hartman, Proc. Natl. Acad. Sci., USA 85:8047, (1988)); mannose-6-phosphate isomerase which allows cells to utilize mannose (International Patent Application No. WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, (1995)).

Additional selectable markers include, for example, a mutant acetolactate synthase, which confers imidazolinone or sulfonylurea resistance (Lee et al., EMBO J. 7:1241-1248, (1988)), a mutant psbA, which confers resistance to atrazine (Smeda et al., Plant Physiol. 103:911-917, (1993)), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, (1983)); streptomycin (Jones et al., Mol. Gen. Genet. 210:86-91, (1987)); spectinomycin (Bretagne-Sagnard et al., Transgenic Res. 5:131-137, (1996)); bleomycin (Hille et al., Plant Mol. Biol. 7:171-176, (1990)); sulfonamide (Guerineau et al., Plant Mol. Biol. 15:127-136, (1990)); bromoxynil (Stalker et al., Science 242:419-423, (1988)); glyphosate (Shaw et al., Science 233:478-481, (1986)); phosphinothricin (DeBlock et al., EMBO J. 6:2513-2518, (1987)), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al., Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Schaller et al., Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al., Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al., (2004) J. Cell Science 117: 943-54 and Kato et al., (2002) Plant Physiol 129: 913-42), the yellow fluorescent protein gene (PHI-YFP™ from Evrogen; see Bolte et al., (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al., (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech. (1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

In certain embodiments, the nucleotide sequence can be optionally combined with another nucleotide sequence of interest. The term "nucleotide sequence of interest" refers to a nucleic acid molecule (which may also be referred to as a polynucleotide) which can be a transcribed RNA molecule as well as DNA molecule, that encodes for a desired polypeptide or protein, but also may refer to nucleic acid molecules that do not constitute an entire gene, and which do not necessarily encode a polypeptide or protein (e.g., a promoter). For example, in certain embodiments the nucleic acid molecule can be combined or "stacked" with another that provides additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through targeted integration via homologous recombination.

Such nucleotide sequences of interest include, but are not limited to, those examples provided below:

1. Genes or Coding Sequence (e.g. iRNA) That Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium flavum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al., (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in *Diploptera punctata* (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, (1992) Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., (1993) Insect Molec. Biol. 23:691), and parsley ubi4-2 polyubiquitin gene (Kawalleck et al., (1993) Plant Molec. Biol. 21:673).

(K) A molecule that stimulates signal transduction. Examples of such molecules include nucleotide sequences for mung bean calmodulin cDNA clones (Botella et al., (1994) Plant Molec. Biol. 24:757) and a nucleotide sequence of a maize calmodulin cDNA clone (Griess et al., (1994) Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., (1993) Plant Sci. 89:43) which renders transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al., (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al., (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavladoraki et al., (1993) Nature 266:469, which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., (1992) Bio/Technology 10:1436). The cloning and characterization of a gene which encodes a bean endopolygalacturonase-inhibiting protein is described by (Toubart et al., (1992) Plant J. 2:367).

(R) A developmental-arrestive protein produced in nature by a plant, such as the barley ribosome-inactivating gene that provides an increased resistance to fungal disease (Longemann et al., (1992). Bio/Technology 10:3305).

(S) RNA interference, in which a DNA polynucleotide encoding an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al., U.S. Pat. No. 6,573,099.

2. Genes that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., (1988) EMBO J. 7:1241), which is also known as AHAS enzyme (Miki et al., (1990) Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (glyphosate oxidase) and other phosphono compounds such as glufosinate (pat and bar genes; DSM-2), and aryloxyphenoxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European Patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricin acetyl-transferase gene is provided in European Patent application No. 0 242 246. De Greef et al., (1989) Bio/Technology 7:61 describes the production of transgenic plants that express chimeric bar genes coding for phosphinothricin acetyl transferase activity. Exemplary of genes conferring resistance to aryloxyphenoxypropionic acids and cyclohexanediones, such as sethoxydim and haloxyfop, are the Accl-S1, Accl-S2 and Accl-S3 genes described by Marshall et al., (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al., (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al., (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxyphenylpyruvate (HPP) is transformed into homogentisate. This includes herbicides such as isoxazoles (European Patent No. 418175, European Patent No. 470856, European Patent No. 487352, European Patent No. 527036, European Patent No. 560482, European Patent No. 682659, U.S. Pat. No. 5,424,276), in particular isoxaflutole, which is a selective herbicide for maize, diketonitriles (European Patent No. 496630, and European Patent No. 496631), in particular 2-cyano-3-cyclopropyl-1-(2-SO2CH3-4-CF3 phenyl) propane-1,3-dione and 2-cyano-3-cyclopropyl-1-(2-SO2CH3-4-2,3Cl2phenyl) propane-1,3-dione, triketones (European Patent No. 625505, European Patent No. 625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Publication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxygenase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-dependent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosystem II reaction centers (PS II) (See Brussian et al., (1989) EMBO J. 1989, 8(4): 1237-1245.

3. Genes That Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., (1992) Proc. Nat. Acad. Sci. USA 89:2624.

(B) Decreased phytate content (1) Introduction of a phytase-encoding gene, such as the *Aspergillus niger* phytase gene (Van Hartingsveldt et al., (1993) Gene 127:87), enhances breakdown of phytate, adding more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., (1990) Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., (1988) J. Bacteriol. 170: 810), *Bacillus subtilis* levansucrase gene (Steinmetz et al., (1985) Mol. Gen. Genel. 200:220), *Bacillus licheniformis* α-amylase (Pen et al., (1992) Bio/Technology 10:292), tomato invertase genes (Elliot et al., (1993), barley amylase gene (Sogaard et al., (1993) J. Biol. Chem. 268:22480), and maize endosperm starch branching enzyme II (Fisher et al., (1993) Plant Physiol. 102:10450).

Described herein are methods of identifying the presence of a donor DNA polynucleotide inserted within a targeted genomic loci. As a further embodiment a site specific nuclease can be used to cleave an unmodified endogenous plant genomic locus, a previously targeted plant genomic locus, or a previously inserted exogenous DNA. The targeting of an endogenous genomic loci is one embodiment of the disclosure.

In embodiments, the methods and compositions described herein make use of a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-30 3388; Dujon et al. (1989) *Gene* 82:115-118; Perler et al. (1994) Nucleic Acids Res. 22, 11127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 5 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) *Science* 337, p. 816-821, Jinek et al, (2013), eLife 2:e00471, and David Segal, (2013) eLife 2:e00563). Thus, the CRISPR/Cas system can be engineered to create a double-stranded break (DSB) at a desired target in a genome, and repair of the DSB can be influenced by the use of repair inhibitors to cause an increase in error prone repair.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. The Cas protein is deployed in mammalian cells (and putatively within plant cells) by co-expressing the Cas nuclease with guide RNA. Two forms of guide RNAs can be ued to facilitate Cas-mediated genome cleavage as disclosed in Le Cong, F., et al., (2013) *Science* 339(6121):819-823.

In certain embodiments, the DNA binding domain of one or more of the nucleases used for in vivo cleavage and/or targeted cleavage of the genome of a cell comprises a zinc finger protein. In some embodiments, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Selection of target sites; ZFPs and methods for design and construction of fusion proteins (and polynucleotides encoding same) are known to those of skill in the art and described in detail in U.S. Pat. Nos. 6,140,815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Thus, the site specific nuclease comprises a DNA-binding domain that specifically binds to a target site in any gene into which it is desired to insert a donor DNA polynucleotide (i.e. comprising at least one transgene).

Any suitable cleavage domain can be operatively linked to a DNA-binding domain to form a nuclease fusion protein. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALEN DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a different nuclease or a TALEN DNA-binding domain and a cleavage domain from a different nuclease, or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al., (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Application Publication WO 07/014275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter.

A "target" or "target site" or "targeted genomic locus" is a nucleic acid sequence that defines a portion of a nucleic acid to which a binding molecule (e.g. site specific nuclease) will bind, provided sufficient conditions for binding exist.

In an embodiment a genomic locus sequence includes those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic locus sequences can be normal (i.e., wild-type) or mutant; mutant sequences can comprise, for example, insertions (e.g., previously inserted exogenous polynucleotides), deletions, translocations, rearrangements, and/or point mutations. A genomic locus sequence can also comprise one of a number of different alleles.

Also described herein as an embodiment of the invention are methods for inserting a donor DNA polynucleotide sequence within a genomic loci. Reported and observed frequencies of targeted genomic modification indicate that targeting of a genomic loci within plants is relatively inefficient. The success rate of such methods are low, due in part to poor efficiency of homologous recombination and a high frequency of non-specific insertion of the donor DNA into regions of the genome other than the target site. The present disclosure provides methods for identifying a donor DNA polynucleotide within a targeted genomic loci The methods of the subject disclosure involve making and using site specific nucleases (e.g., engineered zinc finger binding domains fused to cleavage domains) to make one or more targeted double-stranded breaks in cellular DNA. Because double-stranded breaks in cellular DNA stimulate cellular repair mechanisms several thousand-fold in the vicinity of the cleavage site, such targeted cleavage allows for the alteration or replacement (via homology-directed repair) of sequences at virtually any site in the genome.

In addition to the fusion molecules described herein, targeted replacement of a selected genomic sequence also requires the introduction of the replacement or donor DNA polynucleotide sequence. The donor DNA polynucleotide sequence can be introduced into the cell prior to, concurrently with, or subsequent to, expression of the fusion protein(s). The donor DNA polynucleotide contains sufficient homology to a genomic sequence to support homologous recombination (or homology-directed repair) between it and the genomic sequence to which it bears homology. Approximately 25, 50 100, 200, 500, 750, 1,000, 1,500, 2,000 nucleotides or more of sequence homology between a donor DNA polynucleotide and a genomic locus (or any integral value between 10 and 2,000 nucleotides, or more) will support homologous recombination therebetween. Donor DNA polynucleotide sequences can range in length from 10 to 5,000 nucleotides (or any integral value of nucleotides therebetween) or longer. It will be readily apparent that the donor DNA polynucleotide sequence is typically not identical to the genomic sequence that it replaces. For example, the sequence of the donor DNA polynucleotide can contain one or more single base changes, insertions, deletions, inversions or rearrangements with respect to the genomic sequence, so long as sufficient homology with chromosomal sequences is present. Alternatively, a donor DNA polynucleotide sequence can contain a non-homologous sequence flanked by two regions of homology. Additionally, donor DNA polynucleotide sequences can comprise a vector molecule containing sequences that are not homologous to the region of interest in cellular chromatin. Generally, the homologous region(s) of a donor DNA polynucleotide sequence will have at least 50% sequence identity to a genomic locus with which recombination is desired. In certain embodiments, 60%, 70%, 80%, 90%, 95%, 98%, 99%, or 99.9% sequence identity is present. Any value between 1% and 100% sequence identity can be present, of depending upon the length the donor DNA polynucleotide.

A donor DNA polynucleotide molecule can contain several, discontinuous regions of homology to cellular chromatin. For example, for targeted insertion of sequences not normally present in a region of interest, said sequences can be present in a donor DN polynucleic acid molecule and flanked by regions of homology to sequence in the region of interest.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl Acad. Sd. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor DNA polynucleotide can be introduced into a cell as part of a vector molecule having additional sequences such as, for example, replication origins, promoters and genes encoding antibiotic resistance. Moreover, donor DNA polynucleotides can be introduced as naked nucleic acid, as nucleic acid complexed with an agent such as a liposome or poloxamer or can be delivered by bacteria or viruses (e.g., *Agrobacterium* sp., *Rhizobium* sp. NGR234, *Sinorhizoboium meliloti, Mesorhizobium loti*, tobacco mosaic virus, potato virus X, cauliflower mosaic virus and cassava vein mosaic virus. See, e.g., Chung et al. (2006) Trends Plant Sd. 11(1): 1-4)

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular {e.g., genomic or chromosomal) sequence; i.e., by a processes of homology-directed repair, also known as "gene conversion." Applicants' methods advantageously combine the powerful targeting capabilities of engineered ZFPs with a cleavage domain (or cleavage half-domain) to specifically target a double-stranded break to the region of the genome at insertion of exogenous sequences is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 1,000, 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor DNA polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, members of the RAD52 epistasis group (e.g., Rad50, Rad51, Rad51B, RadSIC, RadSID, Rad52, Rad54, Rad54B, Mrell, XRCC2, XRCC3), genes whose products interact with the aforementioned gene products (e.g., BRCA1, BRCA2) and/or genes in the NBS1 complex. See, e.g., Boyko et al. (2006) Plant Physiology 141:488-497 and LaFarge et al. (2003) Nucleic Acids Res 31(4): 1148-1155. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) EMBO 21:2819-2826; Freisner et al. (2003) Plant J. 34:427-440; Chen et al. (1994) European Journal of Biochemistry 224: 135-142. Methods for activation and repression of gene expression using fusions between a zinc finger binding domain and a functional domain are disclosed, for example, in co-owned U.S. Pat. Nos. 6,534,261; 6,824,978 and 6,933,113. Additional repression methods include the use of anti-sense oligonucleotides and/or small interfering RNA (siRNA or RNAi) targeted to the sequence of the gene to be repressed.

The genetic manipulations of a recombinant host disclosed herein can be performed using standard genetic techniques in any host cell that is suitable to genetic manipulation. In some embodiments, a recombinant host cell disclosed herein can be any organism or microorganism host useful for genetic modification and recombinant gene expression. In some embodiments, a recombinant host can be but is not limited to any higher plant, including both dicotyledonous and monocotyledonous plants, and consumable plants, including crop plants and plants used for their oils. Thus, any plant species or plant cell can be selected as described further below.

In some embodiments, plants which comprise a donor DNA polynucleotide inserted within a targeted genomic locus in accordance with the present disclosure (e.g., plant host cells) include, but is not limited to, any higher plants, including both dicotyledonous and monocotyledonous plants, and particularly consumable plants, including crop plants. Such plants can include, but are not limited to, for example: alfalfa, soybeans, cotton, rapeseed (also described as canola), linseed, corn, rice, brachiaria, wheat, safflowers, sorghum, sugarbeet, sunflowers, tobacco and turf grasses. Thus, any plant species or plant cell can be selected. In embodiments, plant cells used herein, and plants grown or derived therefrom, include, but are not limited to, cells obtainable from rapeseed (*Brassica napus*); indian mustard (*Brassica juncea*); Ethiopian mustard (*Brassica carinata*); turnip (*Brassica rapa*); cabbage (*Brassica oleracea*); soybean (*Glycine max*); linseed/flax (*Linum usitatissimum*); maize (also described as corn) (*Zea mays*); safflower (*Carthamus tinctorius*); sunflower (*Helianthus annuus*); tobacco (*Nicotiana tabacum*); *Arabidopsis thaliana*; Brazil nut (*Betholettia excelsa*); castor bean (*Ricinus communis*); coconut (*Cocus nucifera*); coriander (*Coriandrum sativum*); cotton (*Gossypium* spp.); groundnut (*Arachis hypogaea*); jojoba (*Simmondsia chinensis*); oil palm (*Elaeis guineeis*); olive (*Olea eurpaea*); rice (*Oryza sativa*); squash (*Cucurbita maxima*); barley (*Hordeum vulgare*); sugarcane (*Saccharum officinarum*); rice (*Oryza sativa*); wheat (*Triticum* spp. including *Triticum durum* and *Triticum aestivum*); and duckweed (*Lemnaceae* sp.). In some embodiments, the genetic background within a plant species may vary.

"Plant parts," as used herein, include any parts of a plant, including, but not limited to, seeds (including mature seeds and immature seeds), a plant cutting, a plant cell, a plant cell culture, a plant organ, pollen, embryos, flowers, fruits, shoots, leaves, roots, stems, explants, etc. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants having the physiological and morphological characteristics of the foregoing inbred plant, and of regenerating plants having substantially the same genotype as the foregoing inbred plant. In an embodiment, the regenerable cells in such tissue cultures will be embryos, protoplasts, meristematic cells, callus, pollen, leaves, anthers, roots, root tips, silk, flowers, kernels, ears, cobs, husks or stalks. Still further, embodiments of the present disclosure provide plants regenerated from the tissue cultures of embodiments of the disclosure.

With regard to the production of plants comprising a donor DNA polynucleotide inserted within a genomic locus, methods for the transformation of plants are well known in the art. For instance, numerous methods for plant transformation have been developed, including biological and physical transformation protocols for dicotyledenous plants as well as monocotyledenous plants (e.g., Goto-Fumiyuki et al., Nature Biotech 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors comprising gene expression cassettes and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

A large number of techniques are available for inserting DNA comprising a gene expression cassette into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or Poly Ethylene Glycol mediated transformation as well as other possible methods.

For example, the DNA construct comprising a gene expression cassette may be introduced directly into the genomic DNA of the plant cell using techniques such as electropration and microinjection of plant cell protoplasts, or the DNA constructs can be introduced directly to plant tissue using biolistic methods, such as DNA particle bombardment (see, e.g., Klein et al. (1987) *Nature* 327:70-73).

Additional methods for plant cell transformation include microinjection via silicon carbide WHISKERS™ mediated DNA uptake (Kaeppler et al. (1990) *Plant Cell Reporter* 9:415-418). Alternatively, the DNA construct can be introduced into the plant cell via nanoparticle transformation (see, e.g., U.S. patent application Ser. No. 12/245,685, which is incorporated herein by reference in its entirety).

Another known method of plant transformation is microprojectile-mediated transformation wherein DNA is carried on the surface of microprojectiles. In this method, the expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Alternatively, gene transfer and transformation methods include, but are not limited to, protoplast transformation through calcium chloride precipitation, poly ethylene glycol (PEG) or electroporation-mediated uptake of DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505).

A widely utilized method for introducing an vector comprising a gene expression cassette into plants is based on the natural transformation system of *Agrobacterium*. Horsch et al., *Science* 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., *Crit. Rev. Plant. Sci.* 10:1 (1991). Descriptions of *Agrobacterium* vector systems and methods for *Agrobacterium*-mediated gene transfer are also available, for example, Gruber et al., supra, Miki et al., supra, Moloney et al., *Plant Cell Reports* 8:238 (1989), and U.S. Pat. Nos. 4,940,838 and 5,464,763.

If *Agrobacterium* is used for the transformation, the DNA to be inserted should be cloned into special plasmids, namely either into an intermediate vector or into a binary vector. Intermediate vectors cannot replicate themselves in *Agrobacterium*. The intermediate vector can be transferred into *Agrobacterium tumefaciens* by means of a helper plasmid (conjugation). The Japan Tobacco Superbinary system is an example of such a system (reviewed by Komari et al., (2006) In: Methods in Molecular Biology (K. Wang, ed.) No. 343: *Agrobacterium* Protocols (2$^{nd}$ Edition, Vol. 1) HUMANA PRESS Inc., Totowa, N.J., pp. 15-41; and Komori et al., (2007) Plant Physiol. 145:1155-1160). Binary vectors can replicate in both *E. coli* and in *Agrobacterium*. They comprise a selection marker gene and a linker or polylinker which are framed by the right and left T-DNA border regions. They can be transformed directly into *Agrobacterium* (Holsters, 1978). The *Agrobacterium* used as host cell is to comprise a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet* 16:357-384; Rogers et al. (1986) Methods Enzymol. 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Following the introduction of the genetic construct comprising a gene expression cassette into plant cells, plant cells can be grown and upon emergence of differentiating tissue such as shoots and roots, mature plants can be generated. In some embodiments, a plurality of plants can be generated. Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed)

and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea mays*.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art.

The term "introduced" in the context of inserting a nucleic acid into a cell, includes transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

The term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another plant. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. In embodiments of the subject disclosure the particular event comprises a donor DNA polynucleotide inserted within a targeted genomic locus.

A "transgene" refers to a gene introduced into the genome of an organism by genetic manipulation in order to alter its genotype.

A "transgenic plant" is a plant having one or more plant cells that contain an expression vector comprising a gene expression cassette. The term "Messenger RNA (mRNA)" refers to the RNA that is without introns and that can be translated into protein by the cell.

As used herein, "insert DNA" refers to the heterologous DNA within the donor DNA polynucleotide comprising a gene expression cassette used to transform the plant material while "flanking DNA" or "junction DNA" can comprise either genomic DNA naturally present in an organism such as a plant, or foreign (heterologous) DNA introduced via the transformation process which is extraneous to the original insert DNA molecule, e.g. fragments associated with the transformation event. A "junction" or "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule.

In an embodiment the disclosure relates to a method to identify the presence of a donor DNA polynucleotide within a targeted genome via an amplification reaction in which an amplicon is generated. The detection of the absence of the amplicon is an indication of whether the genomic loci has been disrupted. In additional embodiments, the presence of an amplicon is an indication that a donor DNA polynucleotide was inserted within the genomic loci.

Various assays can be employed in connection with the amplification reaction of certain embodiments of the disclosure. The following techniques are useful in a variety of situations, and in one embodiment, are useful in detecting the presence of the nucleic acid molecule and/or the polypeptide encoded in a plant cell. For example, the presence of the molecule can be determined in a variety of ways, including using a primer or probe of the sequence. The transgene may be selectively expressed in some tissues of the plant or at some developmental stages, or the transgene may be expressed in substantially all plant tissues, substantially along its entire life cycle. However, any combinatorial expression mode is also applicable.

Amplification of a selected, or target, nucleic acid sequence may be carried out by any suitable means. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "3SR") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques were designed primarily for this sorting out.

As used herein, the term "polymerase chain reaction" and "PCR" generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified.

The term "plurality" is used herein to mean two or more, for example, three, four, five or more, including ten, twenty, fifty or more polynucleotides, nucleic acid probes, and the like.

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

In an embodiment, the amplification reaction is quantified. In other embodiments, the amplification reaction is quantitated using a signature profile, in which the signature profile is selected from the group consisting of a melting temperature or a fluorescence signature profile.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' or 3' end) of the exemplified primers fall within the scope of the subject disclosure. Mutations, insertions, and deletions can be produced in a given primer by methods known to an ordinarily skilled artisan.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar assays are a method of detecting and quantifying the presence of a DNA sequence. Briefly, the genomic DNA sample comprising the targeted genomic locus is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the donor DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the donor DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 µM, less than 4 µM, or less than 2.7 µM.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. The following is provided by way of illustration and not intended to limit the scope of the invention.

EXAMPLES

Example 1

Analysis of Targeted Loci in Maize Callus

Genomic Loci Targeting: The genomic locus for corn event DAS-59132 that was previously disclosed in WO2009100188 METHODS FOR DETECTION OF CORN EVENT DAS-59132, herein incorporated by its entirety, was targeted using a zinc finger nuclease designed to specifically bind and cleave the genomic DNA which makes up this event. The resulting transformants were maintained until an analysis to identify and characterize the disruption of the genomic loci within specific events via an amplification reaction could be completed.

The zinc finger proteins directed against DNA sequences which comprise the genomic locus for DAS-59132 were designed as previously described. See, e.g., Urnov et al. (2005) Nature 435:646-651. The DAS-59132 zinc finger designs were incorporated into vectors encoding a protein having at least one finger with a CCHC structure. See, U.S. Patent Publication No. 2008/0182332. In particular, the last finger in each protein had a CCHC backbone for the recognition helix. The non-canonical zinc finger-encoding sequences were fused to the nuclease domain of the type IIS restriction enzyme, FokI (amino acids 384-579 of the sequence of Wah et al. (1998) Proc. Natl. Acad. Sci. USA 95:10564-10569) via a four amino acid linker and an opaque-2 nuclear localization signal derived from Zea mays to form DAS-59132 zinc-finger nucleases (ZFNs). Expression of the fusion proteins in a bicistronic expression construct utilizing a 2A ribosomal stuttering signal as described in Shukla et al. (2009) Nature 459:437-441 was driven by a relatively strong, constitutive and ectopic promoter such as the CsVMV promoter.

The optimal ZFNs were verified for cleavage activity using a budding yeast based system previously shown to identify active nucleases. See, e.g., U.S. Patent Publication No. 20090111119; Doyon et al. (2008) Nat Biotechnol. 26:702-708; Geurts et al. (2009) Science 325:433. Of the numerous ZFNs that were designed, produced and tested to bind to the putative DAS-59132 genomic polynucleotide target sites, preferred ZFNs were identified as having in vivo activity at high levels, and selected for further experimentation. These ZFNs were characterized as being capable of efficiently binding and cleaving the DAS-59132 genomic polynucleotide target sites in planta.

Plasmid vectors containing ZFN expression constructs of the exemplary zinc finger nucleases, which were identified using the yeast assay, were designed and completed using skills and techniques commonly known in the art. Next, the opaque-2 nuclear localization signal::zinc finger nuclease fusion sequence was paired with the complementary opaque-2 nuclear localization signal::zinc finger nuclease fusion sequence. As such, each construct consisted of a single open reading frame comprised of two opaque-2 nuclear localization signal::zinc finger nuclease fusion sequences separated by the 2A sequence from Thosea asigna virus (Mattion et al. (1996) J. Virol. 70:8124-8127). Expression of the ZFN coding sequence was driven by the highly expressing constitutive Zea mays Ubiquitin 1 Promoter (Christensen et al. (1992) Plant Mol. Biol. 18(4):675-89) and flanked by the Zea mays Per 5 3' polyA untranslated region (U.S. Pat. No. 6,699,984).

A donor construct was designed to integrate into the ZFN cleaved genomic DNA of the DAS-59132 genomic locus. This single gene expression cassette is driven by the Rice Actin1 promoter (Os Act1 promoter)::the phosphinothricin acetyl transferase coding sequence (PAT; U.S. Pat. No. 7,838,733)::and is terminated by the Zea mays lipase 3' untranslated region (ZmLip 3'UTR). In addition, the donor plasmid was designed with 1 kB sequence (homology arms) on either end of the target PAT gene that is homologous to sequence on either end of the ZFN cut site in the DAS-59132 genomic locus. The homology arms served as the substrate that the homologous recombination machinery used to insert the transgene into the genomic ZFN cut site. The various gene elements were assembled in a high copy number pUC based plasmid.

Targeted Integration: Transgenic events were targeted to the endogenous genomic locus of DAS-59132. Constructs as described previously include the donor sequence (pDAB107855) and DAS-59132 ZFN 6 (pDAB105906). Co-transformation of these two plasmids resulted in 854 transgenic PAT events that were screened with the method for identifying the presence of a donor DNA polynucleotide within a targeted genomic locus of the subject disclosure.

Maize callus cells, consisting of 12 mL of packed cell volume (PCV) from a previously cryo-preserved cell line plus 28 mL of conditioned medium was subcultured into 80 mL of GN6 liquid medium in a 500 mL Erlenmeyer flask, and placed on a shaker at 125 rpm at 28° C. This step was repeated two times using the same cell line, such that a total of 36 mL PCV was distributed across three flasks. After 24 hours, the GN6 liquid media was removed and replaced with 72 mL GN6 S/M osmotic medium. The flask was incubated in the dark for 30-35 minutes at 28° C. with moderate agitation (125 rpm). During the incubation period, a 50 mg/mL suspension of silicon carbide WHISKERS™ (Advanced Composite Materials, LLC, Greer, S.C.) was prepared by adding 8.1 mL of GN6 S/M liquid medium to 405 mg of sterile, silicon carbide WHISKERS™.

Following incubation in GN6 S/M osmotic medium, the contents of each flask were pooled into a 250 mL centrifuge bottle. After all cells in the flask settled to the bottom, the content volume in excess of approximately 14 mL of GN6 S/M liquid was drawn off and collected in a sterile 1-L flask for future use. The pre-wetted suspension of WHISKERS™ was mixed at maximum speed on a vortex for 60 seconds, and then added to the centrifuge bottle.

In this example, pDAB107855 (donor sequence) and pDAB105906 (ZFN) plasmid DNA were added to each bottle. Once the plasmid DNA was added, the bottle was immediately placed in a modified RED DEVIL 5400™ commercial paint mixer (Red Devil Equipment Co., Plymouth, Minn.), and agitated for 10 seconds. Following agitation, the cocktail of cells, media, WHISKERS™ and plasmid DNA were added to the contents of a 1 L flask along with 125 mL fresh GN6 liquid medium to reduce the osmoticant. The cells were allowed to recover on a shaker set at 125 rpm for 2 hours. 6 mL of dispersed suspension was filtered onto Whatman #4 filter paper (5.5 cm) using a glass cell collector unit connected to a house vacuum line such that 60 filters were obtained per bottle. Filters were placed onto 60×20 mm plates of GN6 solid medium and cultured at 28° C. under dark conditions for 1 week.

One week post-DNA delivery, filter papers were transferred to 60×20 mm plates of GN6 (1H) selection medium containing a selective agent. These selection plates were incubated at 28° C. for one week in the dark. Following 1 week of selection in the dark, the tissue was embedded onto fresh media by scraping ½ the cells from each plate into a tube containing 3.0 mL of GN6 agarose medium held at 37-38° C.

The agarose/tissue mixture was broken up with a spatula and, subsequently, 3 mL of agarose/tissue mixture was evenly poured onto the surface of a 100×25 mm petri dish containing GN6 (1H) medium. This process was repeated for both halves of each plate. Once all the tissue was embedded, plates incubated at 28° C. under dark conditions for up to 10 weeks. Putatively transformed isolates that grew under these selection conditions were removed from the embedded plates and transferred to fresh selection medium in 60×20 mm plates. If sustained growth was evident after approximately 2 weeks, an event was deemed to be resistant to the applied herbicide (selective agent) and an aliquot of cells was subsequently harvested for genotype analysis. In this example, a large number of events were recovered from the treated bottles. These events were advance for molecular analysis to confirm the integration of a transgene within a genomic locus of Corn Event DAS-59132.

DNA Extraction: Callus tissue samples were collected in 96-well collection plates (Qiagen, Valencia, Calif.) and then lyophilized for 48 hours. Tissue disruption was performed with a KLECKO™ tissue pulverizer (Garcia Manufacturing, Visalia, Calif.) in BIOSPRINT96 AP1™ lysis buffer (Qiagen) with one stainless steel bead. Following tissue maceration, genomic DNA was isolated in high throughput format using the BIOSPRINT96™ plant kit (Qiagen) using the BIOSPRINT96™ extraction robot (Qiagen). A sample of genomic DNA was then diluted to 2 ng/µl prior to setting up the qPCR reactions to achieve appropriate Cp (quantification cycle) scores which resulted in the production of a signature profile.

DAS-59132 Locus Disruption Assay: WHISKERS™ mediated transformation of Hi-II callus cells with the DAS-59132-ZFN and donor plasmid resulted in targeted and random transgene insertions. To distinguish random insertion events from the targeted event populations, all 854 events generated were initially screened using a locus disruption assay. This assay determined whether the ZFN binding site within the locus remains intact or had been disrupted through ZFN cleavage or donor insertion. Indication of a disruption within the genomic loci is initial evidence that the ZFN has cleaved the endogenous DAS-59132 target locus and indicates targeted insertion of the donor DNA molecule. Primers were designed to amplify the endogenous target region that contains the ZFN recognition sites, and samples were set up to be analyzed by qPCR. Amplification of the intact region, indicative of an untargeted event, resulted in a 140 base pair amplicon measured as a detectable qPCR signal. Successful targeted integration of the donor molecule results in disruption of the detectable qPCR signal and is shown as a lower overall signal compared to control.

The DAS-59132 locus disruption assay was performed by real-time PCR using the LIGHTCYCLER®480 system (Roche Applied Science, Indianapolis, Ind.). Assays were designed to monitor the DAS-59132 ZFN (25716/25717) binding sequences at the DAS-59132 locus (and the internal reference gene IVF (Genbank Acc No: U16123.1|ZMU16123) using LIGHTCYCLER® Probe Design Software 2.0. For amplification, LIGHTCYCLER®480 Probes Master mix (Roche Applied Science, Indianapolis, Ind.) was prepared at 1× final concentration in a 10 µL volume multiplex reaction containing 0.4 µM of each primer and 0.2 µM of each probe (Table 1). A two step amplification reaction was performed with an extension at 55° C. for 30 seconds with fluorescence acquisition. Analysis for the disruption assay was performed using target to reference ratio.

TABLE 1

Oligonucleotide Primer and Probe Sequences for DAS-59132 Locus Disruption Assay.

| Primer Name | SEQ ID NO: | Sequence | Detection |
|---|---|---|---|
| MAS604 | SEQ ID NO: 1 | ACACGGCACACACGGCGACATTCA | — |
| MAS606 | SEQ ID NO: 2 | AGGGCAGTGGCCAGTGTTCCTGTG | — |
| UPL 69 | — | Roche Sequence | FAM |
| IVF-Taq | SEQ ID NO: 3 | TGGCGGACGACGACTTGT | — |
| IVR-Taq | SEQ ID NO: 4 | AAAGTTTGGAGGCTGCCGT | — |
| IV-Probe | SEQ ID NO: 5 | CGAGCAGACCGCCGTGTACTTCTACC | HEX |

Figure 2:
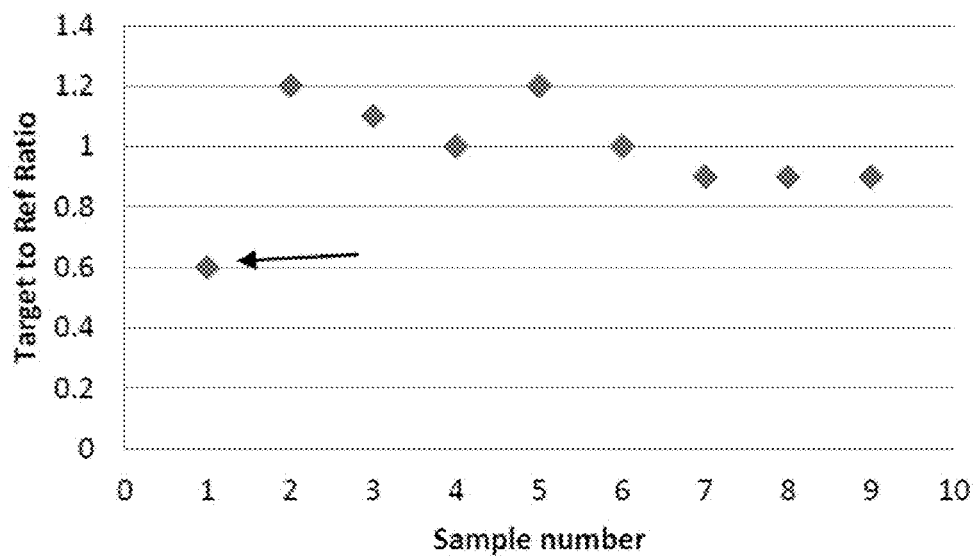
FIG. 2 depicts the results of a ZFN quantitative PCR (qPCR) disruption assay at a targeted locus: screening results of a subset of events. The arrow indicates a transgenic event with a disrupted locus as evidenced by drop in detectable qPCR signal.

The 854 events generated from precision transformation were screened with the disruption assay, and scored as disrupted based on a significant drop in the target to reference signal. The results indicated that 63 of the 854 events assayed had a disrupted signal at the DAS-59132 locus, indicative of targeted gene insertion (FIG. 2). Despite the quantitative measurement of a disrupted locus that the disruption assay provides, this assay cannot resolve targeted insertions from mutations at the cleavage site resulting from error prone break repair. The development of a secondary In-Out PCR assay for screening events in parallel to ensure robust and accurate evaluation of all events was developed.

Figure 3:
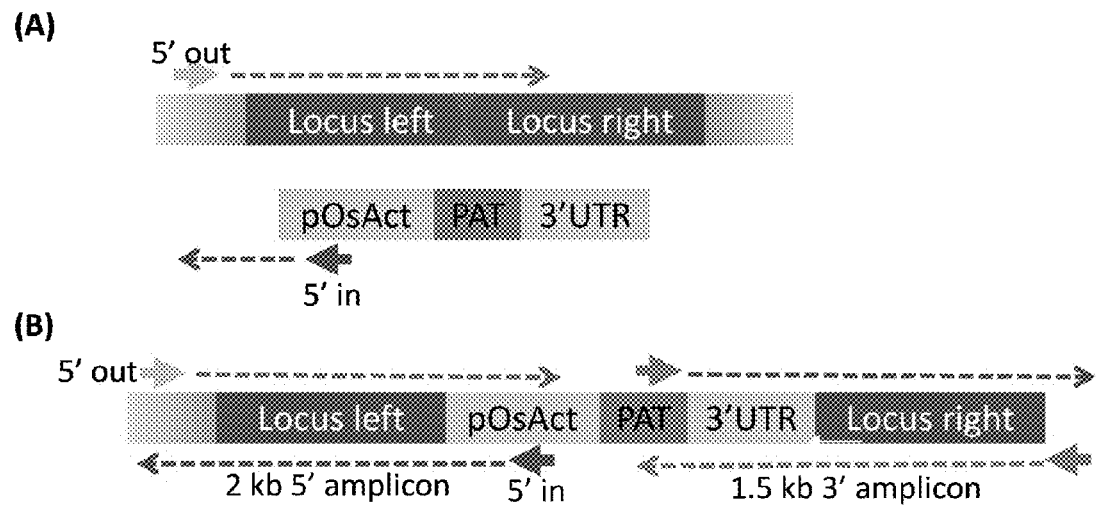
FIG. 3 depicts the screening which is completed with the In-Out PCR amplification process.

DAS-59132 Locus In-Out PCR Assay: The events screened by the disruption assay were also screened by a locus specific end-point PCR assay at the DAS-59132 locus. One oligonucleotide primer is designed to anneal to a region of target genomic DNA outside the ZFN cleavage site and a second oligonucleotide primer is designed to anneal only to the transgene region of the donor DNA. The primers are designed to analyze the 5' and 3' insert DNA junction regions of the target site at the DAS-59132 locus. Many of the events generated from transformation are random insertions and so are not amplified during the In-Out PCR, as the donor sequence is not in proximity to the target sequence (FIG. 3A). As the primers are designed to only amplify regions of donor DNA and genomic DNA that are inserted in the targeted region, amplification is a result of a targeted transgene event (FIG. 3B). This PCR analysis, called "In-Out" PCR, ensures that a complete picture of targeted gene insertion is obtained, as the primers are designed to target both the target sequence and inserted donor sequence and both the 5' and 3' junctions are analyzed. Following PCR, amplified samples are analyzed by electrophoresis and samples with transgene integration at the target site in the DAS-59132 locus result in amplification of two bands at 2 kb and 1.5 kb. This is indicative of integrated target sequence at the 5' and 3' junctions of the transgene.

In-Out PCR amplification reactions were conducted using a Takara Ex Taq HS Kit™ (Clontech Laboratories, Inc., Mountain View, Calif.). Each PCR reaction was carried out in 15 or 20 µL final volume, which contained 1×Ex Taq buffer, 200 nM of forward and reverse primers, 10 to 20 ng of genomic DNA template, and a final concentration of 0.05 unit/µL Ex Taq HS polymerase. For real-time In-Out PCR, a SYTO13® dye from Invitrogen (Grand Island, N.Y.) was included in the PCR reaction mix at a final concentration of 4 µM or 2.67 µM. Initially the SYTO13® green fluorescent dye was used per manufacturer recommended concentrations as it had been previously shown to increase overall assay sensitivity and exhibit low inhibition of polymerase activity. This dye resulted in a stronger signal and more consistent results, but the high-throughput system still had limitations. Background fluorescence continued to be problematic, as primer-dimer formations or non-specific primer annealing (from impure primers) were generating false positive signals. As such, the concentrations which were used in the assay were lower from 10 µM to 4 µM or 2.67 µM. The reduction in concentration of the dye resulted in a signature profile that provided reliable detection and quantitation of the PCR assay.

Real-time In-Out PCR was performed on an ABI VIIA7 PCR SYSTEM™ (Life Technologies Corporation, Carlsbad, Calif.). After initial denaturing, the amplification program contained 40 cycles of 98° C. for 10 sec, 66° C. for 30 sec and 68° C. for 2 min with fluorescence acquisition before a melting temperature analysis program. Following the amplification step, the reaction was kept at 65° C. for 30 sec and 72° C. for 10 min, and finally held at 4° C. Both direct fluorescence signals and melting temperature profiles were used for sample analysis. Positive samples identified on the real-time system were further confirmed using a standard gel shift assay.

TABLE 2

Primer and Probe Sequences for DAS-59132 Locus In Out Assay.

| | Primer Name | SEQ ID NO: | Primer Sequence |
|---|---|---|---|
| 5' Junction Sequence | E32-5F3 | SEQ ID NO: 6 | GAAGGCAAAACGAATATAAG TGCATTCGG |
| | E32-OLP-R1 | SEQ ID NO: 7 | TCGTGGATAGCACTTTGGGCT |

TABLE 2-continued

Primer and Probe Sequences for DAS-59132 Locus In Out Assay.

| | Primer Name | SEQ ID NO: | Primer Sequence |
|---|---|---|---|
| 3' Junction Sequence | E32-OLP-F3 | SEQ ID NO: 8 | TCTACAGTGAACTTTAGGACA GAGCCA |
| | E32-3R2 | SEQ ID NO: 9 | GCCCTTACAGTTCATGGGCG |

Figure 4A:
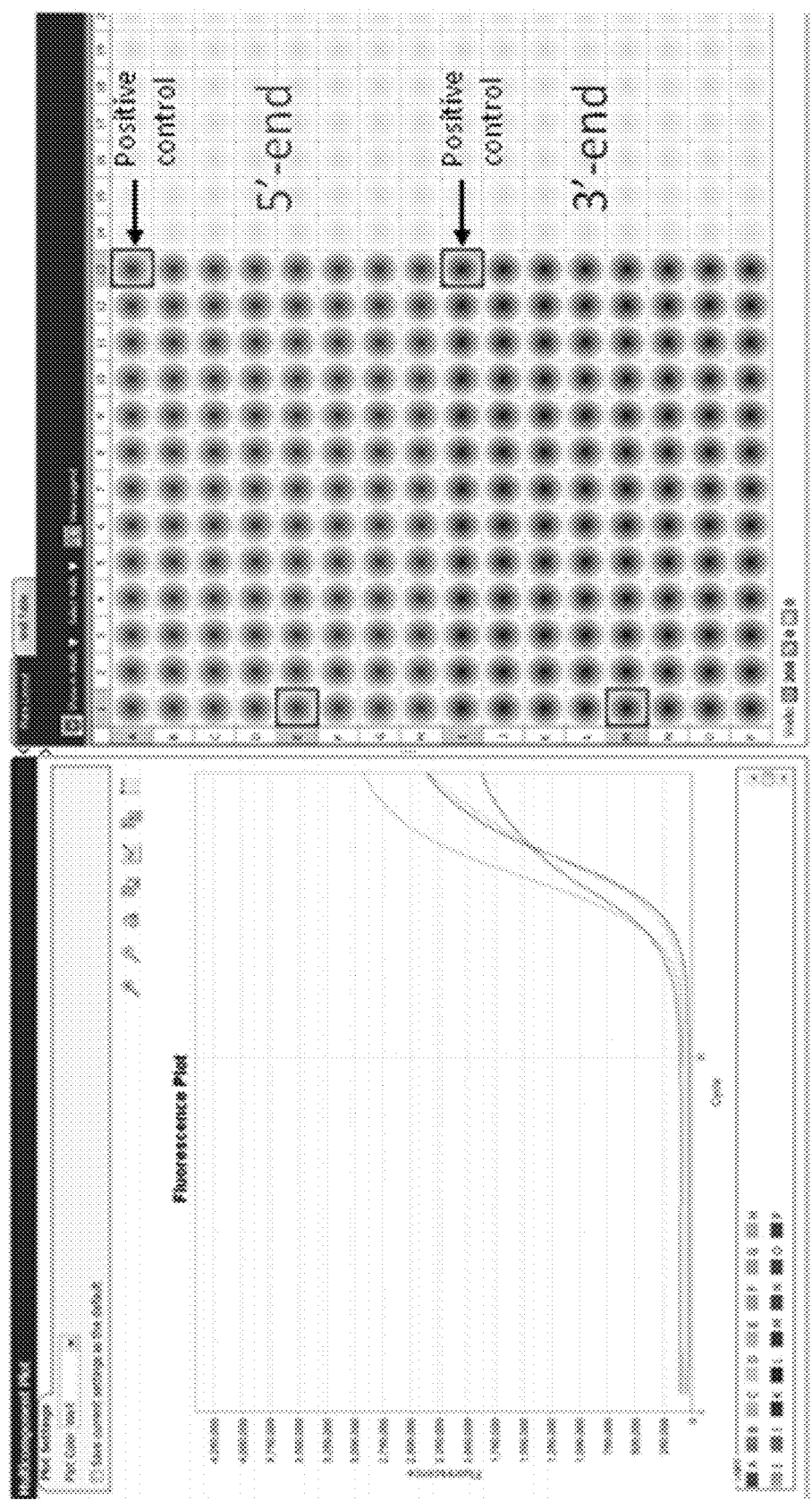
FIGS. 4A and 4B depict an In-Out PCR analysis.
Figure 4B:
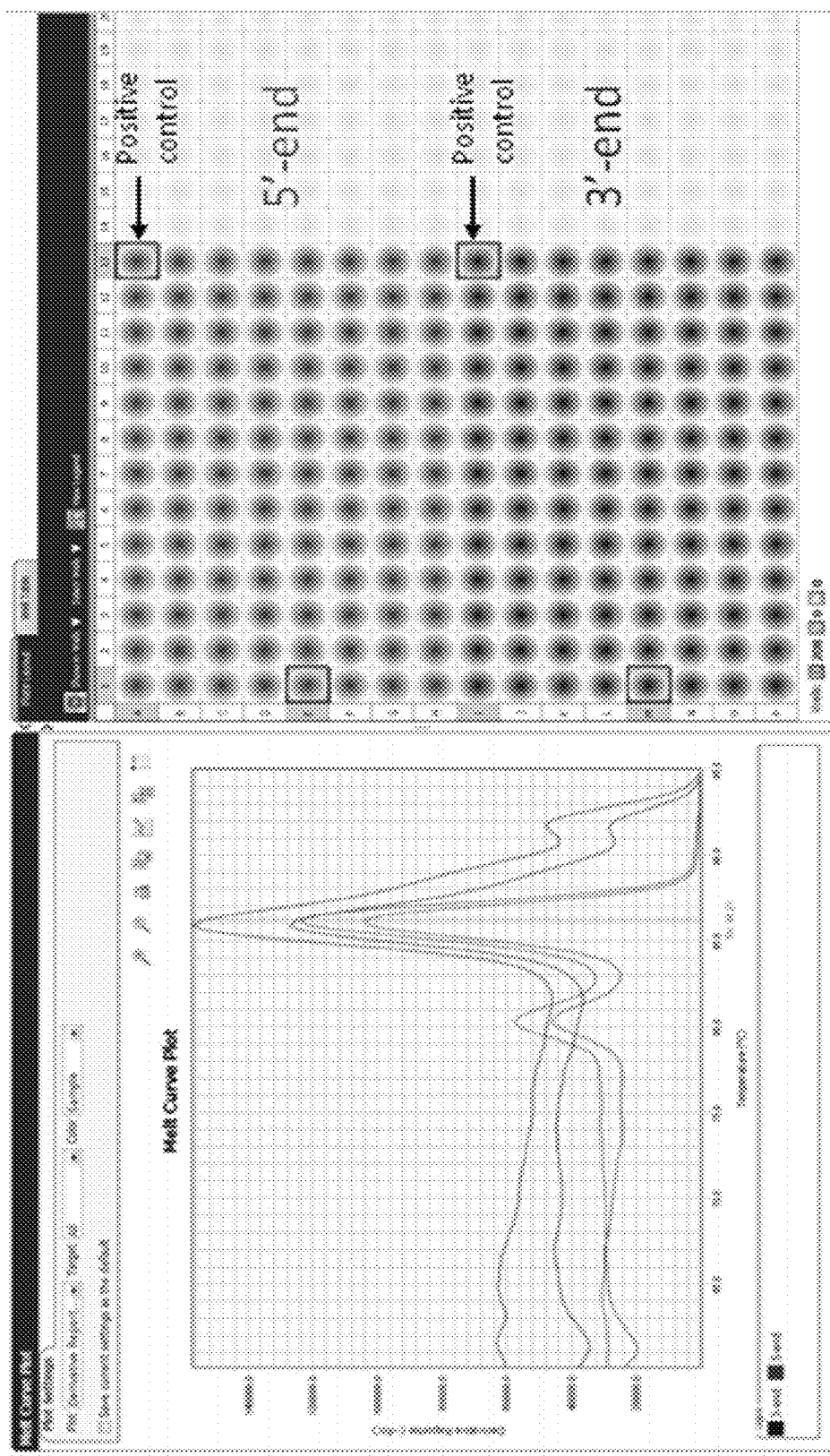

In an effort to differentiate targeted insert PCR amplicons from false positives, a protocol was designed to assign a signature profile to every PCR product generated. Melting temperature profiles of the PCR amplicons were compared to a positive control, and matching curves identified positive In-Out PCR products (FIGS. 4A and 4B). Correlating the In-Out PCR analysis using a signature profile that comprises a melting temperature profile of both the both the 3' and 5' ends is a novel analytical methodology that generates greater confidence in identifying a targeted donor DNA polynucleotide insertion event within a genomic locus.

The results of the disruption assay and the DAS-59132 locus In-Out PCR assay were further confirmed via Southern blotting and sequencing (standard of Next Generation Sequencing).

The novel assay resulted in a robust analytical process to identify targeted donor DNA polynucleotide insertion events at a ZFN cleavage site in maize. The endogenous genomic loci was successfully targeted and the targeted events were efficiently identified using the novel assay. A total of 854 samples were submitted for the analysis using the disclosed assay. The disruption assay was performed on all of the putative events with 63 of the events showing disruption. The In-Out PCR was performed on all of the events, and 8 positive events were identified. As a result, there were a total of 8 events that were confirmed to be targeted inserts (FIG. 5).

Example 2

Analysis of Targeted Loci in Maize Plants

Maize transgenic B104 embryos were generated, wherein the DAS-59132 locus was targeted via the Zinc Finger Nuclease construct, pDAB105906, and a donor construct, pDAB104179. These constructs were transformed into the plant tissue using a biolistic transformation method as described in Example 7 of US Patent Application No. 2011/0191899, herein incorporated by reference in its entirety. Putatively transformed embryos were identified via selection of the herbicide phosphinothricin.

Figure 6:
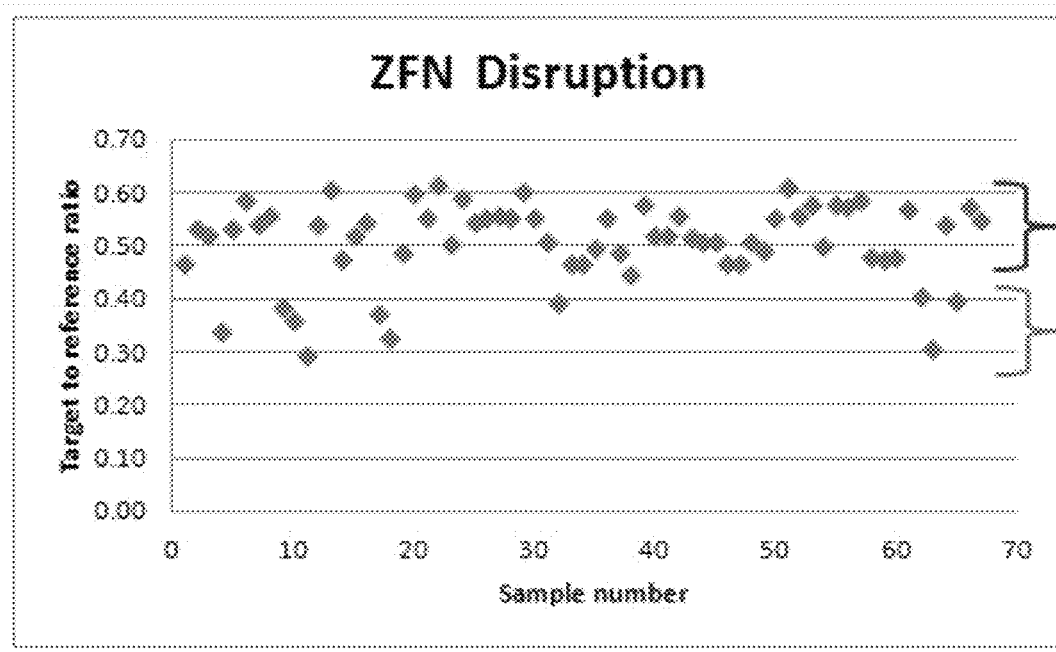
FIG. 6 depicts a ZFN disruption assay. Samples shown in the top bracket do not contain a disrupted genomic locus and samples shown in the bottom bracket do contain a disrupted genomic locus.

The putatively identified transgenic embryos were analyzed using the disruption assay to identify events which contained the presence of a donor DNA polynucleotide inserted within a targeted genomic locus. The ZFN disruption assay was completed using the protocols and reagents described above. In the events that were not targeted or disrupted, a target to reference ratio in the 0.4 to 0.6 range was observed; for samples that were disrupted or targeted a range from 0.2 to 0.35 (plate to plate variation) was reported (FIG. 6). The targeted events which did not produce an amplicon resulted in a lower quantity of amplified product, as depicted in the graph.

Next, locus specific In-Out PCR was completed using the protocol and reagents described above. The results of the In-Out PCR identified specific events which contained a transgene insertion within the DAS-59132 locus.

A total of 1,223 sample events were submitted for the analysis. The disruption assay was completed on every event, and identified 85 of the events showing disruption. The In-Out PCR was completed on all 1,223 sample events and identified 11 events that were positive and 2 partial positive events. Southern blotting and sequencing was completed to confirm that the identified events comprised full transgene insertions within the DAS-59132 genomic locus.

Example 3

Analysis of Targeted Loci in Maize Plants

Maize transgenic B104 embryos were generated, wherein an engineered landing pad locus (US Patent Application No. 2011/0191899, herein incorporated by reference in its entirety) was targeted via the Zinc Finger Nuclease and a donor construct were transformed into the plant tissue using biolistics. Multiple transformations were completed to target a donor construct within the engineered landing pad locus. The first series of transformations were completed using the pDAB109714 donor construct and the pDAB105941 Zinc Finger Nuclease construct. A second series of transformations were completed using the pDAB109715 donor construct and the pDAB105943 Zinc Finger Nuclease construct. A third series of transformations were completed using the pDAB109716 donor construct and the pDAB105942 Zinc Finger Nuclease construct. The final series of transformations were completed using the pDAB109717 donor construct and the pDAB105945 Zinc Finger Nuclease construct. Putatively transformed embryos were identified via selection of the herbicide phosphinothricin.

ELP Locus Disruption Assay: Primers were designed to amplify the endogenous target region that contains the ZFN recognition sites, and samples were set up to be analyzed by qPCR. Amplification of the intact region, indicative of an untargeted event, resulted in a 193 base pair amplicon measured as a detectable qPCR signal. Successful targeted integration of the donor molecules within the respective ELP event results in disruption of the detectable qPCR signal and is shown as a lower overall signal compared to control.

The ELP locus disruption assay was performed by real-time PCR using the LIGHTCYCLER®480 system (Roche Applied Science, Indianapolis, Ind.). Assays were designed to monitor the ELP ZFN binding sequences at the ELP locus, and the internal reference gene IVF using LIGHTCYCLER® Probe Design Software 2.0). For amplification, LIGHTCYCLER®480 Probes Master mix (Roche Applied Science, Indianapolis, Ind.) was prepared at 1× final concentration in a 10 μL volume multiplex reaction containing 0.4 μM of each primer and 0.2 μM of each probe (Table 3). A two step amplification reaction was performed with an extension at 55° C. for 30 seconds with fluorescence acquisition. Analysis for the disruption assay was performed using target to reference ratio.

TABLE 3

Primer and Probe Sequences for ELP Locus Disruption Assay. The ELP1 and ELP2 reactions were multiplexed with the IVF primers and probe, the sequences of which are described in Table 1.

| | Primer Name | SEQ ID NO: | Sequence | Detection |
|---|---|---|---|---|
| ELP1 | MAS622 | SEQ ID NO: 10 | TAGGAGTTCTCTTTTATGCCACCC | — |
| | MAS621 | SEQ ID NO: 11 | CCTTGGGATTTCAGTTGGTAGGTT | — |
| | UPL69 | — | Roche Sequence | FAM |
| ELP2 | MAS617 | SEQ ID NO: 12 | TGGGTAGGAGGACACCAAAGATGA | — |
| | MAS 618 | SEQ ID NO: 13 | CCATTGGATTATTGAAAACTGGCAG | — |
| | UPL122 | — | Roche Sequence | FAM |

Figure 7:
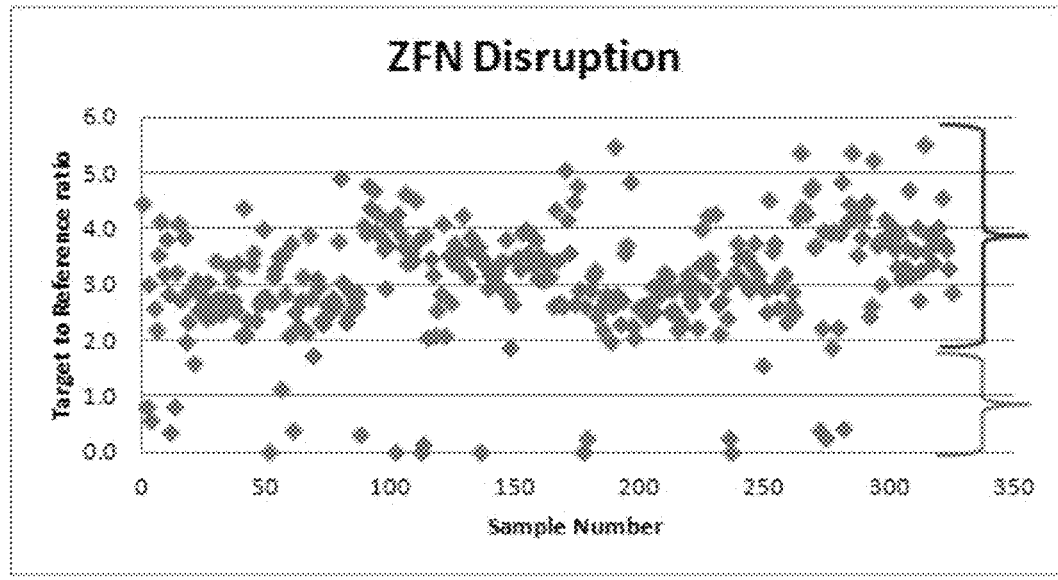
FIG. 7 depicts another ZFN disruption assay. Samples shown in the top bracket do not contain a disrupted genomic locus and samples shown in the bottom bracket do contain a disrupted genomic locus.

The 1738 events generated from precision transformation were screened with the disruption assay, and scored as disrupted based on a significant drop in the target to reference signal. The results indicated that 158 of the 1738 events assayed had a disrupted signal at the ELP locus, indicative of targeted gene insertion (FIG. 7). Despite the quantitative measurement of a disrupted locus that the disruption assay provides, this assay does not resolve targeted insertions from mutations at the cleavage site resulting from error prone break repair. Therefore, the development of a secondary In-Out PCR assay for screening events in parallel to ensure robust and accurate evaluation of all events was developed.

ELP Loci In-Out PCR Assay: The events screened by the disruption assay were also screened by a newly-developed locus specific end-point PCR assay at the ELP loci. One primer was designed to anneal to a region of target genomic DNA outside the ZFN cleavage site and a second primer was designed to anneal only to the transgene region of the donor DNA. The primers were designed to analyze the 5' and 3' regions of the target site at the ELP locus. As the primers were designed to only amplify regions of donor DNA and genomic DNA that are inserted in the targeted region, amplification is a result of a targeted transgene event, both of the 5' and 3' junctions were analyzed.

In-Out PCR amplification reactions were conducted using a TAKARA EX TAQ HS KIT™ (Clontech Laboratories, Inc., Mountain View, Calif.). Each PCR reaction was carried out in 15 or 20 μL final volume, which contained 1×Ex Taq buffer, 200 nM of forward and reverse primers, 10 to 20 ng of genomic DNA template, and a final concentration of 0.05 unit/μL Ex Taq HS polymerase. For real-time In-Out PCR, a SYTO13® dye (Invitrogen, Carlsbad, Calif.) was included in the PCR reaction mix at a final concentration of 4 μM or 2.67 μM.

Real-time In-Out PCR was performed on an ABI VIIA7 PCR SYSTEM™ (Life Technologies Corporation, Carlsbad, Calif.). After initial denaturing, the amplification program contained 40 cycles of 98° C. for 10 sec, 66° C. for 30 sec and 68° C. for 2 min with fluorescence acquisition before a melting temperature analysis program. Following that, the reaction was kept at 65° C. for 30 sec and 72° C. for 10 min, and finally held at 4° C. Both direct fluorescence signals and melting temperature profiles were used for sample analysis.

Positive samples identified on the real-time system were further confirmed using a standard gel shift assay.

TABLE 4

Primer and Probe Sequences for ELP Locus In Out Assay.

| Primer Name | SEQ ID NO: | Primer Sequence |
|---|---|---|
| 5' Junction Sequence | ELP1-PriF1 | SEQ ID NO: 14 | AGA CCT ACC ACC CAT TAG GGC |
| | OsAct-PriR3 | SEQ ID NO: 15 | TCG TGG ATA GCA CTT TGG GCT |
| 3' Junction Sequence | AAD1-PriF1 | SEQ ID NO: 16 | CTT GAC TCG CAC CAC AGT TGG |
| | ELP2-PriR1 | SEQ ID NO: 17 | GAT GGT GGT TAT GAC AGG CTC CT |

In an effort to identify PCR amplicons from false positives, a protocol was designed to assign a signature profile to every PCR product generated. Melting temperature profiles of the PCR amplicons were compared to a positive control, and matching curves identified positive In-Out PCR products. Correlating the In-Out PCR analysis using a signature profile that comprises a melting temperature profile of both the both the 3' and 5' ends is an analytical methodology that generates greater confidence in identifying a targeted transgene insertion event.

A total of 1738 PAT positive samples were submitted for this project. The disruption assay and the In-Out PCR was performed on all events. The results indicated that 158/1738 events were positive for disruption, and 46/1738 of these events were positive for both the 3' and 5' In-Out PCR amplification reactions.

Example 4

Analysis of Targeted Loci in Maize Plants

*Zea mays* c.v. B104 plants were transformed with an engineered landing pad gene construct (pDAB105817 or pDAB105818) as previously described in US Patent Application No. 2011/0191899. Transformed maize plants were obtained and confirmed to contain the ELP. Four ELP maize lines; 105817[1]-015.Sx001.Sx011, 105818[1]-269.Sx001.Sx008, 105818[1]-271.Sx001.Sx005, and 105818[2]-388.Sx001.Sx008 were crossed with *Zea mays* c.v. B104 to produce as hemizygotes. The resulting progeny plants were co-transformed with either eZFN plasmid pDAB105941 encoding eZFN1 and corresponding donor plasmid pDAB104182 or eZFN pDAB105948 encoding eZFN8 and donor pDAB104183. The transformations were completed via bombardment of isolated embryos that were shot one time using a PDS-1000 (Bio-Rad) per manufacturer's specifications. A total of 20,896 embryos (about 5000 embryos for each target line) were bombarded and selected for Bialaphos resistance: 12,404 were co-bombarded with pDAB105941 and its corresponding donor, and 8,492 embryos were co-bombarded with pDAB105948 and its corresponding donor.

Following bombardment, embryos were cultured in media and grown into plantlets. Transgenic events were identified via a qPCR that was developed to screen and detect the presence of the pat transgene. The copy number were determined by comparison of Target/Reference (Invertase) values for unknown samples (output by the LightCycler 480™) to Target/Reference values of known copy number standards (1-Copy: hemi, 2-Copy: homo). A total of 614 regenerated plants survived, and 354 (or 58%) of the plants were identified as positive for the presence of the pat gene and retained for further analysis.

ELP Locus Disruption Assay: A ZFN disruption assay was designed to monitor the changes in the integrated ELP. In a non-targeted ELP, PCR primers MAS621 and MAS622 (Table 5) amplified a 214 bp product encompassing the eZFN binding sites. Integration into (or modification of) the eZFN binding site at the ELP locus would disrupt amplification using qPCR with low extension time resulting in either no signal or significantly lower signal being produced in the qPCR reaction. A control qPCR reaction for the amplification of the Invertase gene was also included as an internal control reference.

For amplification, LightCycler®480 Probes Master mix (Roche Applied Science, Indianapolis, Ind.) was prepared at 1× final concentration in a 10 μL volume multiplex reaction containing 0.4 μM of each primer and 0.2 μM of each probe. A three step amplification reaction was performed with 10 seconds at 95° C. for denaturation, 35 seconds at 60° C. for annealing and 1 second at 72° C. with fluorescence acquisition. The FAM fluorescent moiety was excited at an optical density of 465/510 nm and HEX at 533/580 nm. The copy number was determined by comparison of Target/Reference (Invertase) values for unknown samples (output by the LightCycler 480™) to Target/Reference values of known single copy hemizygotes.

Figure 8:
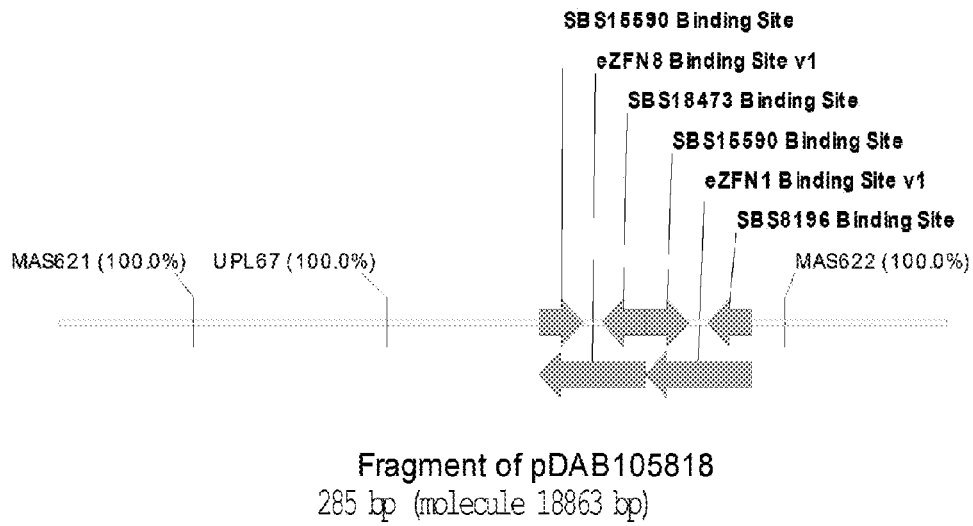
FIG. 8 depicts an eZFN disruption assay at the ELP locus region.
Figure 8:
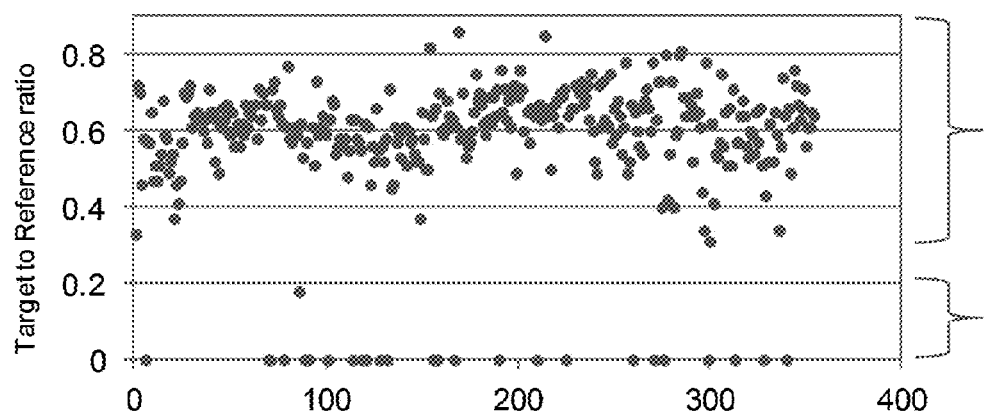

To distinguish random insertion events from ELP-targeted events, the 354 samples that were identified via the pat qPCR screening were further analyzed using the disruption assay. The ELP disruption assay was designed to monitor the large insertions/deletions in the eZFN cleavage site. In a non-targeted ELP, a 214 bp PCR product encompassing the eZFN binding sites is amplified and generates strong fluorescent signals. Integration into (or modification of) the eZFN binding site would disrupt amplification and result in either no signal or significantly lower levels of fluorescent signal produced via the PCR reaction. Out of the 354 pat positive events, about 8% (28 events) appeared to be disrupted (FIG. 8b), indicating potential targeting.

TABLE 5

Primer and probe used for disruption assay.

| Primer Name | SEQ ID NO: | Sequence | |
|---|---|---|---|
| MAS621 | SEQ ID NO: 18 | CCTTGGGATTTC AGTTGGTAGGTT | Disruption assay |
| UPL67 | — | Roche Sequence | |
| MAS622 | SEQ ID NO: 19 | TAGGAGTTCTCT TTTATGCCACCC | |
| InvertaseF | SEQ ID NO: 20 | TGGCGGACGACGA CTTGT | Invertase |
| InvertaseProbe | SEQ ID NO: 21 | Hex-CGAGCAGAC CGCCGTGTACTT | Reference gene |
| InvertaseR | SEQ ID NO: 22 | AAAGTTTGGAGGC TGCCGT | |

In-Out PCR: The disruption assay identified changes in the eZFN binding region on the ELP. Any variation in the primer binding sites or random insertions in the locus are possible indications of disruption to the locus that is caused by ZFN cleavage. Next, an In-Out PCR was used to validate the presence of a donor insertion within the ELP locus. The both ends of the junction sequences comprising the target locus and the donor. One primer was designed to anneal to a pre-integrated ELP region only present in the target lines and a second primer was designed to anneal only to donor DNA sequences that are only present within the donor construct. Amplification via PCR indicated a result of targeting of the donor within the ELP genomic locus. Any events generated from random insertions do not produce a PCR amplification.

For the donor/ELP 5' junction In-Out PCR, the forward primer was designed to bind the OsAct1 region (5OsF3, SEQ ID NO:23 ATTTCACTTTGGGCCACCTT) of the donor insert, while the reverse primer (5R3, SEQ ID NO:24 AGGCTCCGTTTAAACTTGCTG) was designed to bind the 193 bp sequence unique to the target line in the ELP Left Arm. For the 3' donor/ELP locus junction In-Out PCR, the forward primer (3PAF1, SEQ ID NO:25 ATGGTGGATG-GCATGATGTT) was designed to bind the in the PATv6 region of the donor insert, and the reverse primer (3R1, SEQ ID NO:26 TGGAGGTTGACCATGCTAGG) was designed to bind the 192 bp sequence unique to the target line in the ELP Right Arm. Amplification resulted only when the forward and reverse primers bound to sequences in close proximity of one another. Random integration of the donor sequences was not detectable using the above described PCR primers. To increase the throughput of the In-Out PCR detection, the melting curve analysis was completed with the green fluorescent nucleic acid stain, SYTO13®. The PCR amplification was performed on LightCycler 480™ real time PCR system in a 15 µl reaction containing 0.75 units of TaKaRa Ex Taq™ DNA polymerase (Takara Bio Inc., Shiga, Japan), 200 nM of dNTP, 200 nM each of forward and reverse primers, 2.67 µM of SYTO13® and 10 ng of genomic DNA. Amplification started with a 2 min. denaturing cycle at 95° C., then 30 cycles of 98° C. for 20 seconds, 60° C. for 30 seconds and 68° C. for 90 seconds, followed by melting curve analysis at 97° C. with 0.11° C./s ramp speed.

Figure 9:
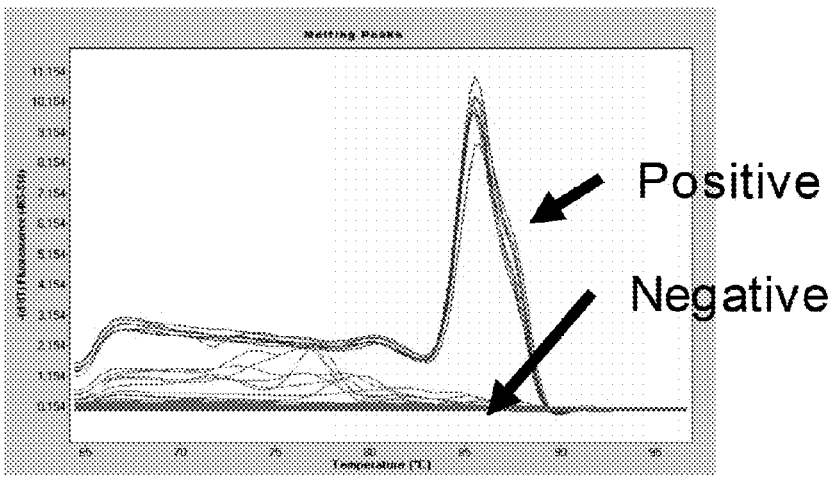
FIG. 9 depicts an In-Out PCR analysis.
Figure 9:
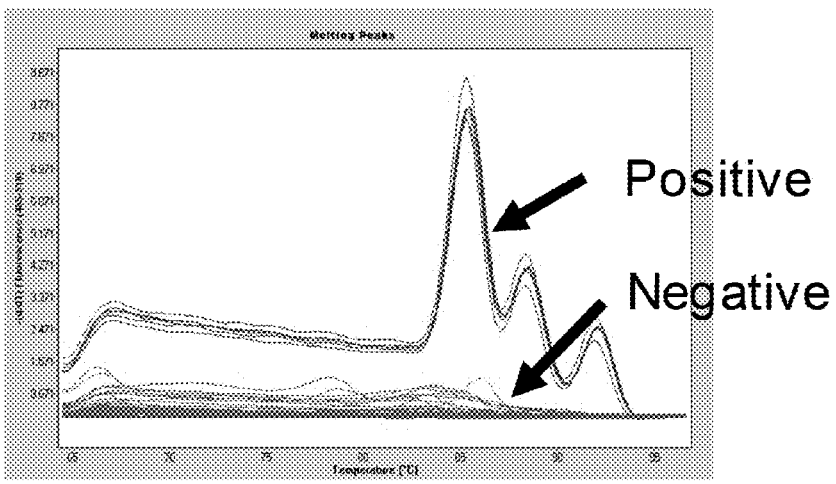

The results of the PCR reaction resulted in the analysis of both the 5' and 3' flanking ends. A donor targeted ELP locus event results in a 1.1 kb fragment for the 5' In-Out PCR reaction and a 1.4 kb fragment for the 3' In-Out PCR reaction. The results of the PCR reactions were determined via melting curve analysis, which produces different graphical results depending on the length and composition of the amplicon (FIG. 9). Short PCR amplicons usually display a single-peak melting temperature (Tm) curve that appears as a flat line and produces low-levels of fluorescent signal when displayed graphically. But for long amplicons (i.e., 1-2 kb fragments), the Tm profile appears more complex, and results in multiple peaks (depending on local sub-sequences of the amplicons) and produces high-levels of fluorescent signal. Five events were identified to be positive for both the 5' and 3' PCR reactions. Each of the four target lines produced an event comprising a donor inserted within the ELP genomic locus. All of the In-Out PCR positives were run on gel where they only showed one band of PCR amplicon, as expected.

Molecular Confirmation: Additional molecular detection methods were completed to confirm that the results of the disruption assay and In-Out PCR reactions were not false positives. A Southern blot analysis and sequencing of the 5' and 3' donor insert/ELP genomic locus junctions were completed. The results confirmed that the events identified via the disruption assay and In-Out PCR analysis contained a donor insert within the ELP genomic locus.

Example 5

Analysis of Disrupted Loci in Maize Plants

Delivery of ZFNs to a genomic locus of a target line plant were introduced via a plant crossing strategy as previously disclosed in US Pat. Pub. No. 20110191877. Separate target and excisor plant events were generated in Zea mays c.v. B104. Five lines of target plants were produced from transformations with constructs pDAB105816, pDAB105817, pDAB105818, pDAB105820, and pDAB105821. These constructs contained a stack of transgenes, an aad-1 selectable marker gene, and an ELP containing the eZF1 and eZF8 binding sites. Next, two lines of excisor plants were produced from transformation with constructs pDAB105828 and pDAB105825. The pDAB105828 construct contained ZFN8 driven by the Zea mays Ubiquitin 1 promoter and terminated by Zea mays Per5 3'UTR. The pDAB105825 construct contained ZFN1 driven by the Zea mays Ubiquitin 1 promoter and terminated by Zea mays Per5 3'UTR. Both of the excisor constructs also contained a pat selectable marker. Transgenic plants were produced and confirmed via molecular confirmation assays. The plants were selfed to produce homozygous progeny. The resulting homozygous target and excisor events were crossed producing progeny. The progeny were assayed to determine if the ZFN transgene provided by the parent excisor event cleaved the ELP target locus provided by the other parent target event. The majority of all crosses were made with target lines as females and excisor lines as males. Only one control cross was made with the excisor line as a female and the target line as a male. The target and excisor plants were crossed to produce progeny that were screened by applying Assure II™ (quizalofop) (184 g ae/ha+1% COC) and Ignite™ 280 SL (glufosinate) (480 gae/ha) at the V3 stage of development. Any surviving progeny were selected for further molecular analysis that entailed screening for the presence of an aad-1 transgene via a qPCR method. A total of 1902 samples were genotyped for the presence of aad-1 locus using a qPCR assay utilizing invertase as the reference gene. The aad-1 target to reference ratios were calculated and normalized to known standards, where a ratio of 2, 1, or 0 indicated homozygosity, hemizygosity, or null status respectively. 1822 plants were confirmed as aad-1 hemizygous.

Figure 10:
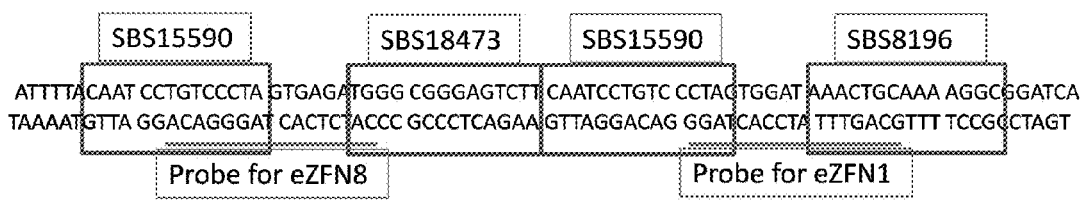
FIG. 10 provides an illustration of ZF binding sequences with corresponding zinc fingers and hydrolysis probes for use in the ELP locus disruption assay: the eZFN8 line represents the probe for detection of activities from eZFN8 with spacer GTGAGA in between binding site sequences SBS15590 and SBS18473; and the eZFN1 line represents the probe for detection of activities from eZFN1 with spacer GTGGAT in between the second set of binding site sequences, SBS15590 and SBS8196. The top sequence is provided as SEQ ID NO:39 and the complementary sequence shown in the bottom of the figure is provided as SEQ ID NO:40.

ZFN disruption assay: A PCR based disruption assay was designed for an indirect measurement of ZFN cutting activity of the ELP target genomic locus. The assays were designed such that the fluorescently labeled probes sat on top of the spacer required for the integrity of the ZFN functions (FIG. 10). The eZFN1 disruption assay resulted in the detection of a 69 bp fragment covering the entire eZFN1 binding site sequence. The eZFN8 disruption assay resulted in the detection of a 109 bp fragment flanking the eZFN8 binding site sequence. Both assays utilize MGB probes synthesized by Life Technologies (Grand Island, N.Y.). When ZFNs cleaved the ELP genomic locus the cleavage was repaired via NHEJ which resulted in the incorporation of InDels within the genomic sequences, thereby modifying the genomic sequence which had been used for design of PCR primers. As a result any PCR amplification reactions designed to amplify and detect an amplicon over the ZFN binding sequence within the ELP genomic locus would not produce a fluorescent signal (as the genomic sequences would be deleted or rearranged, and the primers could not bind these genomic sequences).

Figure 11:
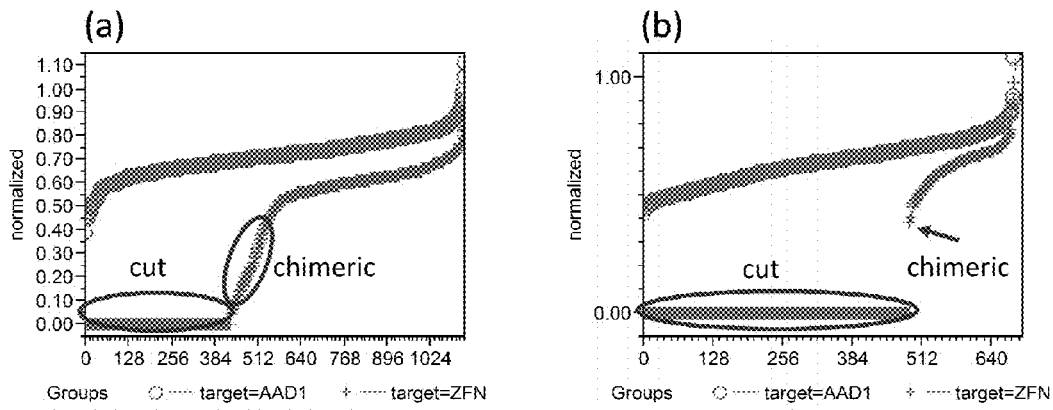
FIG. 11 illustrates an overlay plot of normalized aad-1 (in circles) and ELP copy number (in addition signs).

Bi-plex assays were performed with real-time or qPCR using the LightCycler®480 system (Roche Applied Science, Indianapolis, Ind.). A control reaction was completed with Invertase used as an endogenous reference gene. For amplification, LightCycler®480 Probes Master mix (Roche Applied Science, Indianapolis, Ind.) was prepared at 1× final concentration in a 10 µL volume multiplex reaction containing 0.4 µM of each primer and 0.2 µM of each probe (Table 6). A three-step amplification reaction started with 10 seconds at 95° C. for denaturation, 35 seconds at 60° C. for annealing and 1 second at 72° C. for fluorescence acquisition. Analysis for the disruption assay was performed using target to reference ratios and normalized to known homozygotes. The results of the PCR assay are provided as FIG. 11.

TABLE 6

Primers used for qPCR detection.

| Name | SEQ ID NO: | Sequence | |
|---|---|---|---|
| ZFN1_F | SEQ ID NO: 27 | TAGTGAGATGG GCGGGAGTCT | For eZFN1 detection |
| ZFN1_P | SEQ ID NO: 28 | CCTAGTGGATA AACTGC | |
| ZFN1_R | SEQ ID NO: 29 | CCCACAGTGAT CCGCCTTT | |
| ZFN8_F | SEQ ID NO: 30 | GCTTCTCTGTGA TGATAACCCCTA | For eZFN8 detection |
| ZFN8_R | SEQ ID NO: 31 | TCCGCCTTTTGC AGTTTATC | |
| ZFN8S_P | SEQ ID NO: 32 | TGTCCCTAGTGA GATG | |
| InvertaseF | SEQ ID NO: 33 | TGGCGGACGACG ACTTGT | Invertase Reference gene |
| InvertaseProbe | SEQ ID NO: 34 | CGAGCAGACCG CCGTGTACTT | |

TABLE 6-continued

Primers used for qPCR detection.

| Name | SEQ ID NO: | Sequence | |
|---|---|---|---|
| InvertaseR | SEQ ID NO: 35 | AAAGTTTGGAG GCTGCCGT | |
| aad-1F | SEQ ID NO: 36 | TGTTCGGTTC CCTCTACCAA | For aad-1 control detection |
| aad-1P | SEQ ID NO: 37 | CACAGAACCGTC GCTTCAGCAACA | |
| aad-1R | SEQ ID NO: 38 | CAACATCCATC ACCTTGACTGA | |

To determine the eZFN cutting rate of the ELP genomic locus, F1 leaf samples from the plant crosses were first analyzed for zygosity and were then tested for ELP disruption using a qPCR assay that detects intact eZFN binding sites. If the ELP genomic locus incurred InDels during DSB repair on the eZF binding site, there was a loss or decrease in detectable signal in the qPCR assay. The normalized ELP ratios were compared to their sister lines. If the ratio was between 0 to 0.05, they were considered as being cut with the ZFN (with imperfect repair); if the ratio was between 0.05 to 0.4, they were labeled as chimeric, indicating not all copies of the ELPs have been cut with the ZFN; if the ratio was over 0.4, they were identified as not being cut with the ZFN (could also have been cut but with perfect repair). Taking both cut and chimeric scoring together, eZFN1 activity detected with the disruption assay was 46.6% (524 out of 1125 plant events) and the activity of eZFN8 was 70.2% (489 out of 697 plant events). (Table 7). Tukey Kramer test revealed significant differences among crosses for the cleavage frequencies. The combination of L2BG and excisor lines proved crucial for the success of cleavage ($p < 0.0001$).

TABLE 7

ZFN cleavage activities among 5 ELP target lines and excisor line progeny.

| Crosses | total | cut | chimeric | no cut | cut rate |
|---|---|---|---|---|---|
| pDAB105821.1.295.1::pDAB105828.1.40.1 | 49 | 35 | 0 | 14 | 71.4% |
| pDAB105821.1.295.1::pDAB105828.1.35.1 | 3 | 2 | 0 | 1 | 66.7% |
| pDAB105821.1.295.1::pDAB105825.1.91.1 | 7 | 3 | 2 | 2 | 71.4% |
| pDAB105821.1.295.1::pDAB105825.1.87.1 | 25 | 13 | 4 | 8 | 68.0% |
| pDAB105821.1.295.1::pDAB105825.1.12.1 | 19 | 8 | 4 | 7 | 63.2% |
| pDAB105821.1.264.1::pDAB105828.1.40.1 | 70 | 63 | 0 | 7 | 90.0% |
| pDAB105821.1.264.1::pDAB105828.1.35.1 | 37 | 30 | 0 | 7 | 81.1% |
| pDAB105821.1.264.1::pDAB105825.1.87.1 | 15 | 3 | 1 | 11 | 26.7% |
| pDAB105821.1.264.1::pDAB105825.1.12.1 | 20 | 17 | 2 | 1 | 95.0% |
| pDAB105820.1.199.1::pDAB105828.1.35.1 | 77 | 55 | 0 | 22 | 71.4% |
| pDAB105820.1.199.1::pDAB105825.1.91.1 | 21 | 16 | 2 | 3 | 85.7% |
| pDAB105820.1.199.1::pDAB105825.1.87.1 | 9 | 2 | 1 | 6 | 33.3% |
| pDAB105828.1.40.1::pDAB105820.1.199.1 | 41 | 30 | 0 | 11 | 73.2% |
| pDAB105820.1.140.1::pDAB105828.1.40.1 | 16 | 15 | 0 | 1 | 93.8% |
| pDAB105820.1.140.1::pDAB105828.1.35.1 | 25 | 8 | 0 | 17 | 32.0% |
| pDAB105820.1.140.1::pDAB105825.1.91.1 | 15 | 15 | 0 | 0 | 100.0% |
| pDAB105820.1.140.1::pDAB105825.1.87.1 | 104 | 15 | 3 | 86 | 17.3% |
| pDAB105820.1.140.1::pDAB105825.1.12.1 | 44 | 5 | 3 | 36 | 18.2% |
| pDAB105818.2.388.1::pDAB105828.1.40.1 | 58 | 52 | 0 | 6 | 89.7% |
| pDAB105818.2.388.1::pDAB105828.1.35.1 | 18 | 10 | 0 | 8 | 55.6% |
| pDAB105818.2.388.1::pDAB105825.1.91.1 | 176 | 110 | 7 | 59 | 66.5% |
| pDAB105818.2.388.1::pDAB105825.1.87.1 | 19 | 5 | 3 | 11 | 42.1% |
| pDAB105818.2.388.1::pDAB105825.1.12.1 | 2 | 2 | 0 | 0 | 100.0% |
| pDAB105818.1.269.1::pDAB105828.1.40.1 | 18 | 14 | 0 | 4 | 77.8% |
| pDAB105818.1.269.1::pDAB105828.1.35.1 | 35 | 23 | 0 | 12 | 65.7% |
| pDAB105818.1.269.1::pDAB105825.1.91.1 | 152 | 29 | 13 | 110 | 27.6% |
| pDAB105818.1.269.1::pDAB105825.1.87.1 | 98 | 21 | 14 | 63 | 35.7% |
| pDAB105818.1.269.1::pDAB105825.1.12.1 | 30 | 14 | 11 | 5 | 83.3% |

TABLE 7-continued

ZFN cleavage activities among 5 ELP target lines and excisor line progeny.

| Crosses | total | cut | chimeric | no cut | cut rate |
|---|---|---|---|---|---|
| pDAB105817.1.81.1::pDAB105828.1.35.1 | 59 | 36 | 0 | 23 | 61.0% |
| pDAB105817.1.81.1::pDAB105825.1.91.1 | 24 | 0 | 0 | 24 | 0.0% |
| pDAB105817.1.81.1::pDAB105825.1.87.1 | 97 | 17 | 8 | 72 | 25.8% |
| pDAB105817.1.81.1::pDAB105825.1.12.1 | 42 | 36 | 5 | 1 | 97.6% |
| pDAB105817.1.6.1::pDAB105828.1.40.1 | 20 | 17 | 0 | 3 | 85.0% |
| pDAB105817.1.6.1::pDAB105828.1.35.1 | 15 | 3 | 0 | 12 | 20.0% |
| pDAB105817.1.6.1::pDAB105825.1.91.1 | 52 | 49 | 1 | 2 | 96.2% |
| pDAB105816.2.496.1::pDAB105828.1.40.1 | 29 | 27 | 1 | 1 | 96.6% |
| pDAB105816.2.496.1::pDAB105828.1.35.1 | 27 | 13 | 0 | 14 | 48.1% |
| pDAB105816.2.496.1::pDAB105825.1.91.1 | 7 | 2 | 1 | 4 | 42.9% |
| pDAB105816.2.496.1::pDAB105825.1.87.1 | 16 | 5 | 0 | 11 | 31.3% |
| pDAB105816.2.496.1::pDAB105825.1.12.1 | 10 | 10 | 0 | 0 | 100.0% |
| pDAB105816.2.447.1::pDAB105828.1.40.1 | 13 | 7 | 0 | 6 | 53.8% |
| pDAB105816.2.447.1::pDAB105828.1.35.1 | 61 | 39 | 0 | 22 | 63.9% |
| pDAB105816.2.447.1::pDAB105825.1.87.1 | 82 | 12 | 5 | 65 | 20.7% |
| pDAB105821.1.309.1::pDAB105828.1.35.1 | 26 | 9 | 0 | 17 | 34.6% |
| pDAB105821.1.309.1::pDAB105825.1.91.1 | 21 | 8 | 4 | 9 | 57.1% |
| pDAB105821.1.309.1::pDAB105825.1.87.1 | 10 | 4 | 1 | 5 | 50.0% |
| pDAB105821.1.309.1::pDAB105825.1.12.1 | 8 | 8 | 0 | 0 | 100.0% |

Figure 12:
FIG. 12A, FIG. 12B, FIG. 12C, FIG. 12D, and FIG. 12E provides a sequence alignment for ELP genomic locus samples cut with eZFN1 (pDAB105825) and eZFN8 (pDAB105828). Polynucleotide spacers between ZFN recognition sites are indicated in red boxes. Bases shown as dashes (-) are deletions representing a minimum of one missing base of the sequence.
Figure 12A:
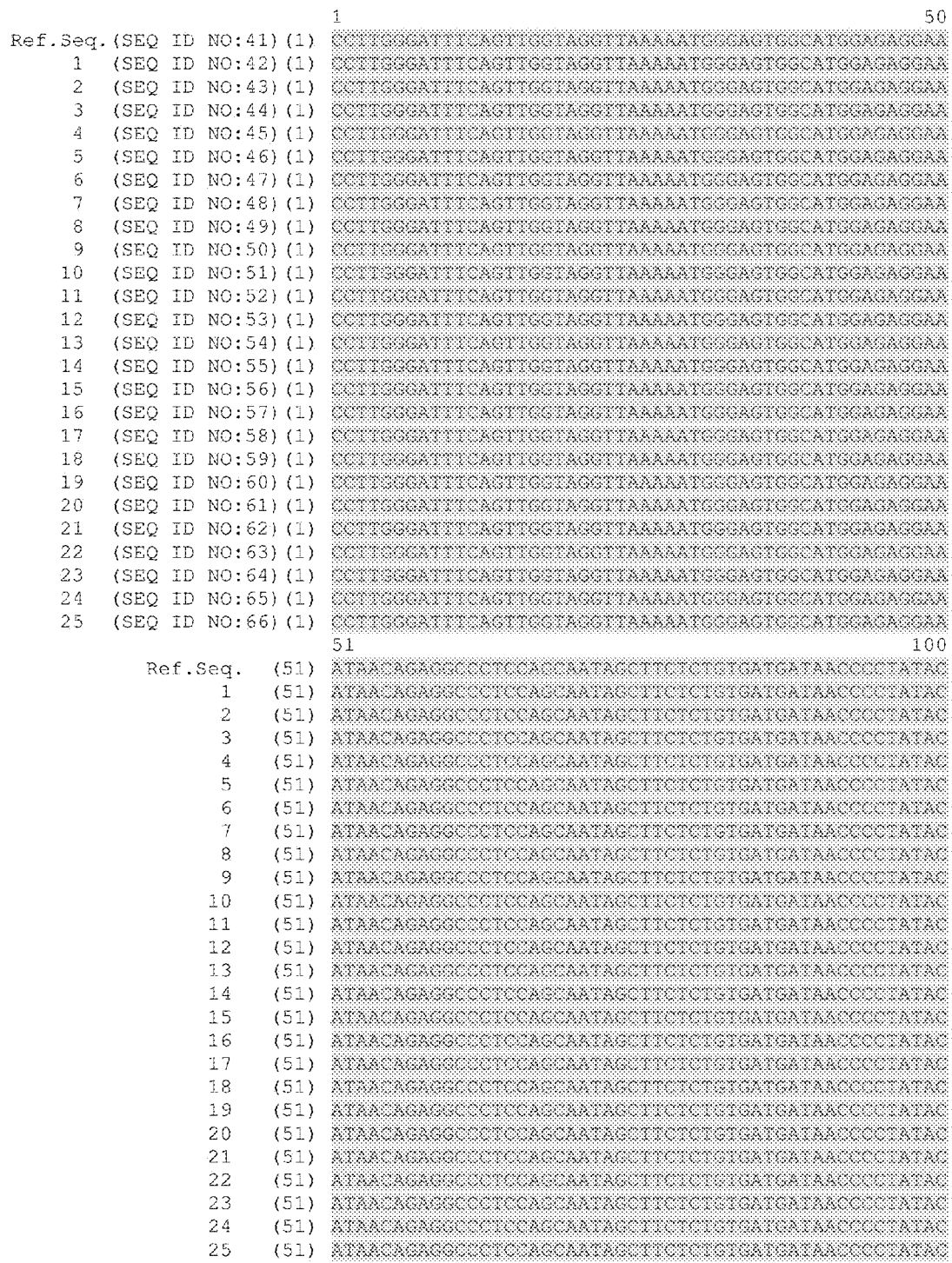
Figure 12B:
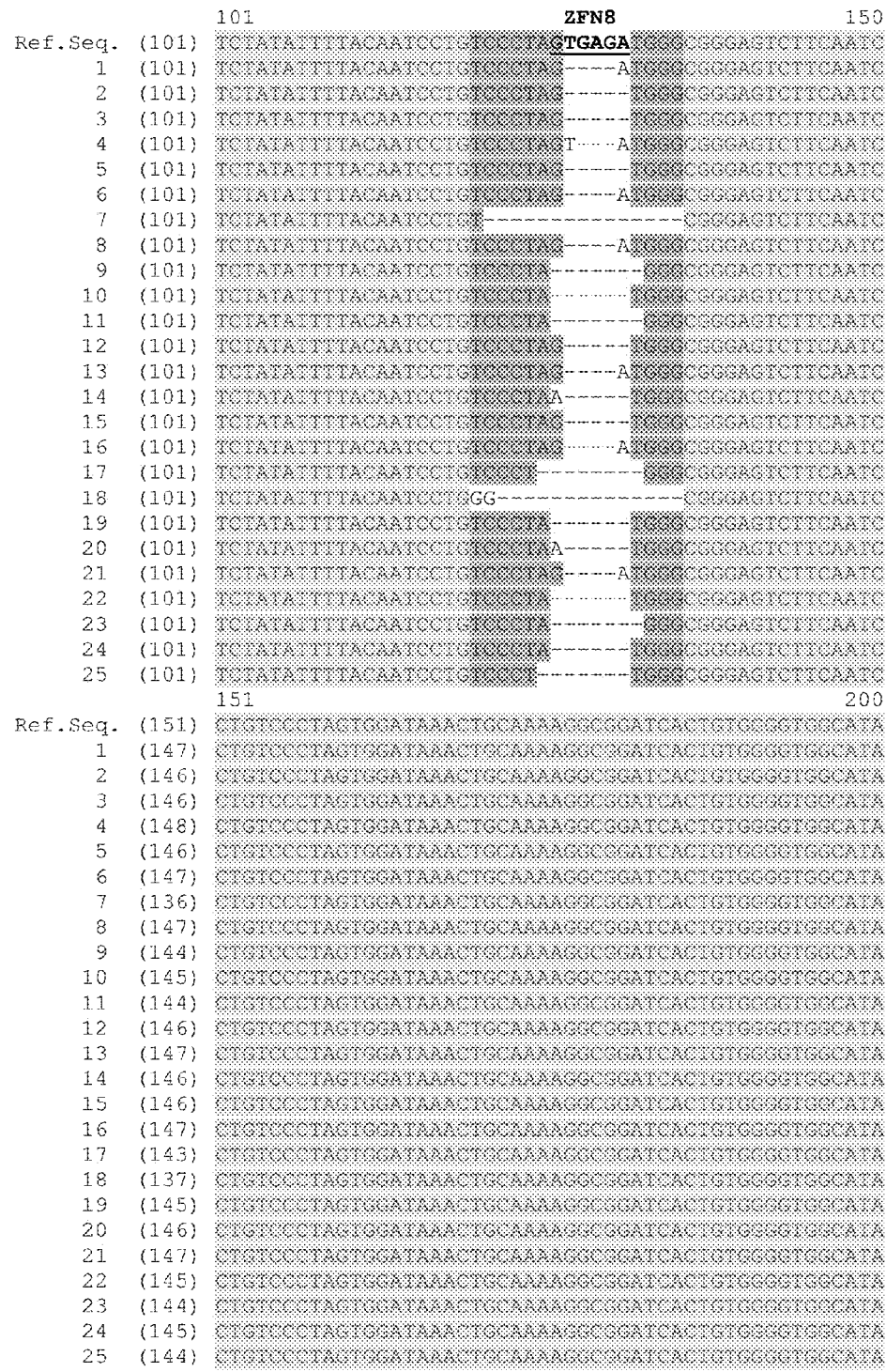

Sequence analysis of ZFN cleavage: To confirm the qPCR based ELP disruption data, representative samples from progeny crosses, and two negative controls represented by the parental target lines were selected for NGS amplicon deep sequencing. High quality reads were aligned against the reference sequence from the ELP construct and insertions and/or deletions (InDels) were identified. As expected, the two parental lines had very small percentage (<0.1%) of indels at the ZFN cleavage site when comparing to the reference sequence, most likely due to PCR amplification and/or sequencing error (FIG. 12). There was a correlation between the qPCR and sequencing data. The four crosses exhibiting 100% cutting efficiencies based on the qPCR data had a 91% or more modified ELPs with sequencing. In summary, NGS deep amplicon sequencing data concurred with the qPCR data and proved the disruption assay method to be highly sensitive. In addition, the ELP disruption assay was demonstrated to be an effective asay for estimating the ZFN (or any other site specific nuclease) cutting activities in planta.

While aspects of this invention have been described in certain embodiments, they can be further modified within the spirit and scope of this disclosure. This application is therefore intended to cover any variations, uses, or adaptations of embodiments of the invention using its general principles. Further, this application is intended to cover such departures from the present disclosure as come within known or customary practice in the art to which these embodiments pertain and which fall within the limits of the appended claims.

What is claimed is:

1. A method for identifying the presence of an exogenous donor DNA polynucleotide inserted within a single targeted eukaryotic genomic locus, the method comprising the following steps:
   a. cleaving the single eukaryotic genomic locus with a site specific nuclease to yield a cleaved eukaryotic genomic locus;
   b. inserting the exogenous donor DNA within the cleaved eukaryotic genomic locus;
   c. amplifying in a first amplification reaction a genomic DNA sample comprising the targeted eukaryotic genomic locus using a first plurality of primers that bind under hybridization conditions proximal to the targeted eukaryotic genomic locus, wherein at least one of the primers binds to the site specific nuclease cleavage site, to thereby generate a first amplicon comprising the targeted eukaryotic genomic locus;
   d. detecting the presence or absence of the first amplicon, wherein the absence of the first amplicon indicates the presence of the exogenous donor DNA polynucleotide within the targeted eukaryotic genomic locus;
   e. amplifying in a second amplification reaction the genomic DNA sample using a second plurality of primers that bind under hybridization conditions proximal to the targeted eukaryotic genomic locus and within the exogenous donor DNA polynucleotide, to thereby generate a second amplicon comprising at least a portion of the targeted eukaryotic genomic locus and at least a portion of the exogenous donor DNA polynucleotide; and,
   f. detecting the presence or absence of the second amplicon, wherein the presence of the second amplicon indicates the presence of the exogenous donor DNA polynucleotide within the targeted eukaryotic genomic locus.

2. The method of claim 1, the method further comprising:
   a. quantitating the results of the first amplification reaction;
   b. quantitating the results of the second amplification reaction;
   c. comparing the results of the first and second amplification reactions; and,
   d. determining the presence or absence of the exogenous donor DNA polynucleotide within the targeted eukaryotic genomic locus, wherein the exogenous donor DNA polynucleotide is confirmed as inserted within the targeted eukaryotic genomic locus if the first amplicon is absent and the second amplicon is present.

3. The method of claim 2, the method further comprising a multiplex reaction, wherein the first and second amplification reactions are run in a single tube or well.

4. The method of claim 2, wherein quantitating the results of the of first and second amplification reactions comprises producing a signature profile for one or both of the first and second amplification reactions.

5. The signature profile of claim 4, wherein the signature profile is selected from the group consisting of a melting temperature curve signature profile and a fluorescence signature profile.

6. The method of claim 4, wherein the signature profile is produced from an intercalating DNA dye.

7. The method of claim 6, wherein the intercalating DNA dye comprises a cyanine dye.

8. The method of claim 7, wherein the cyanine dye is used in an amplification reaction at a concentration of less than 4 µM.

9. The method of claim 7, wherein the cyanine dye is used in an amplification reaction at a concentration of less than 2.7 µM.

10. The method of claim 4, wherein the signature profile is produced from a fluorescent dye.

11. The method of claim 1, the method further comprising:
    a. selecting a transgenic event comprising the exogenous donor DNA polynucleotide within the targeted eukaryotic genomic locus.

12. The method of claim 1, wherein the nuclease comprises a zinc finger nuclease.

13. The method of claim 1, wherein the nuclease comprises a TALEN or CRISPR nuclease.

14. The method of claim 1, wherein the amplifying comprises amplifying in a polymerase chain reaction.

15. The method of claim 1, wherein the second amplicon comprises a 5' junction of the exogenous donor DNA polynucleotide and the targeted eukaryotic genomic locus.

16. The method of claim 1, wherein the second amplicon comprises a 3' junction of the exogenous donor DNA polynucleotide and the targeted eukaryotic genomic locus.

17. The method of claim 1, wherein the exogenous donor DNA polynucleotide comprises at least one gene expression cassette.

18. The method of claim 1, wherein the first or second plurality of primers, or both, comprise a fluorescent dye.

19. The method of claim 18, wherein the fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

20. The method of claim 1, wherein the primers further comprise a probe.

* * * * *

SEQUENCE LISTING

<160> NUMBER OF SEQ ID NOS: 91

<210> SEQ ID NO 1
<211> LENGTH: 24
<212> TYPE: DNA
<213> ORGANISM: Artificial Sequence
<220> FEATURE:
<223> OTHER INFORMATION: MAS604 Primer Sequence

<400> SEQUENCE: 1
acacggcaca cacggcgaca ttca                                      24

<210> SEQ ID NO 2
<211> LENGTH: 24
<212> TYPE: DNA
<213> ORGANISM: Artificial Sequence
<220> FEATURE:
<223> OTHER INFORMATION: MAS606 primer sequence

<400> SEQUENCE: 2
agggcagtgg ccagtgttcc tgtg                                      24

<210> SEQ ID NO 3
<211> LENGTH: 18
<212> TYPE: DNA
<213> ORGANISM: Artificial Sequence

```
<220> FEATURE:
<223> OTHER INFORMATION: IVF-Taq Primer Sequence

<400> SEQUENCE: 3
tggcggacga cgacttgt                                                   18

<210> SEQ ID NO 4
<211> LENGTH: 19
<212> TYPE: DNA
<213> ORGANISM: Artificial Sequence
<220> FEATURE:
<223> OTHER INFORMATION: IVR-Taq Primer Sequence

<400> SEQUENCE: 4
aaagtttgga ggctgccgt                                                  19

<210> SEQ ID NO 5
<211> LENGTH: 26
<212> TYPE: DNA
<213> ORGANISM: Artificial Sequence
<220> FEATURE:
<223> OTHER INFORMATION: IV-Probe Primer Sequence

<400> SEQUENCE: 5
cgagcagacc gccgtgtact tctacc                                          26

<210> SEQ ID NO 6
<211> LENGTH: 29
<212> TYPE: DNA
<213> ORGANISM: Artificial Sequence
<220> FEATURE:
<223> OTHER INFORMATION: E32-5F3 Primer Sequence

<400> SEQUENCE: 6
gaaggcaaaa cgaatataag tgcattcgg                                       29

<210> SEQ ID NO 7
<211> LENGTH: 21
<212> TYPE: DNA
<213> ORGANISM: Artificial Sequence
<220> FEATURE:
<223> OTHER INFORMATION: E32-OLP-R1  Primer Sequence

<400> SEQUENCE: 7
tcgtggatag cactttgggc t                                               21

<210> SEQ ID NO 8
<211> LENGTH: 27
<212> TYPE: DNA
<213> ORGANISM: Artificial Sequence
<220> FEATURE:
<223> OTHER INFORMATION: E32-OLP-F3  Primer Sequence

<400> SEQUENCE: 8
tctacagtga actttaggac agagcca                                         27

<210> SEQ ID NO 9
<211> LENGTH: 20
<212> TYPE: DNA
<213> ORGANISM: Artificial Sequence
<220> FEATURE:
<223> OTHER INFORMATION: E32-3R2 Primer Sequence

<400> SEQUENCE: 9
gcccttacag ttcatgggcg                                                 20
```

```
<210> SEQ ID NO 10
<211> LENGTH: 24
<212> TYPE: DNA
<213> ORGANISM: Artificial Sequence
<220> FEATURE:
<223> OTHER INFORMATION: MAS622 Primer Sequence

<400> SEQUENCE: 10
taggagttct cttttatgcc accc                                          24

<210> SEQ ID NO 11
<211> LENGTH: 24
<212> TYPE: DNA
<213> ORGANISM: Artificial Sequence
<220> FEATURE:
<223> OTHER INFORMATION: MAS621 Primer Sequence

<400> SEQUENCE: 11
ccttgggatt tcagttggta ggtt                                          24

<210> SEQ ID NO 12
<211> LENGTH: 24
<212> TYPE: DNA
<213> ORGANISM: Artificial Sequence
<220> FEATURE:
<223> OTHER INFORMATION: MAS617 Primer Sequence

<400> SEQUENCE: 12
tgggtaggag gacaccaaag atga                                          24

<210> SEQ ID NO 13
<211> LENGTH: 25
<212> TYPE: DNA
<213> ORGANISM: Artificial Sequence
<220> FEATURE:
<223> OTHER INFORMATION: MAS618 Primer Sequence

<400> SEQUENCE: 13
ccattggatt attgaaaact ggcag                                         25

<210> SEQ ID NO 14
<211> LENGTH: 21
<212> TYPE: DNA
<213> ORGANISM: Artificial Sequence
<220> FEATURE:
<223> OTHER INFORMATION: ELP1-PriF1 Primer Sequence

<400> SEQUENCE: 14
agacctacca cccattaggg c                                             21

<210> SEQ ID NO 15
<211> LENGTH: 21
<212> TYPE: DNA
<213> ORGANISM: Artificial Sequence
<220> FEATURE:
<223> OTHER INFORMATION: OsAct-PriR3 Primer Sequence

<400> SEQUENCE: 15
tcgtggatag cactttgggc t                                             21

<210> SEQ ID NO 16
<211> LENGTH: 21
<212> TYPE: DNA
<213> ORGANISM: Artificial Sequence
<220> FEATURE:
<223> OTHER INFORMATION: AAD1-PriF1 Primer Sequence
```

-continued

<400> SEQUENCE: 16
cttgactcgc accacagttg g                                    21

<210> SEQ ID NO 17
<211> LENGTH: 23
<212> TYPE: DNA
<213> ORGANISM: Artificial Sequence
<220> FEATURE:
<223> OTHER INFORMATION: ELP2-PriR1 Primer Sequence

<400> SEQUENCE: 17
gatggtggtt atgacaggct cct                                  23

<210> SEQ ID NO 18
<211> LENGTH: 24
<212> TYPE: DNA
<213> ORGANISM: artificial sequence
<220> FEATURE:
<223> OTHER INFORMATION: primer sequence

<400> SEQUENCE: 18
ccttgggatt tcagttggta ggtt                                 24

<210> SEQ ID NO 19
<211> LENGTH: 24
<212> TYPE: DNA
<213> ORGANISM: artificial sequence
<220> FEATURE:
<223> OTHER INFORMATION: primer sequence

<400> SEQUENCE: 19
taggagttct cttttatgcc accc                                 24

<210> SEQ ID NO 20
<211> LENGTH: 18
<212> TYPE: DNA
<213> ORGANISM: artificial sequence
<220> FEATURE:
<223> OTHER INFORMATION: primer sequence

<400> SEQUENCE: 20
tggcggacga cgacttgt                                        18

<210> SEQ ID NO 21
<211> LENGTH: 21
<212> TYPE: DNA
<213> ORGANISM: artificial sequence
<220> FEATURE:
<223> OTHER INFORMATION: probe sequence

<400> SEQUENCE: 21
cgagcagacc gccgtgtact t                                    21

<210> SEQ ID NO 22
<211> LENGTH: 19
<212> TYPE: DNA
<213> ORGANISM: artificial sequence
<220> FEATURE:
<223> OTHER INFORMATION: primer sequence

<400> SEQUENCE: 22
aaagtttgga ggctgccgt                                       19

<210> SEQ ID NO 23

```
<211> LENGTH: 20
<212> TYPE: DNA
<213> ORGANISM: artificial sequence
<220> FEATURE:
<223> OTHER INFORMATION: primer sequence

<400> SEQUENCE: 23
atttcacttt gggccacctt                                              20

<210> SEQ ID NO 24
<211> LENGTH: 21
<212> TYPE: DNA
<213> ORGANISM: artificial sequence
<220> FEATURE:
<223> OTHER INFORMATION: primer sequence

<400> SEQUENCE: 24
aggctccgtt taaacttgct g                                            21

<210> SEQ ID NO 25
<211> LENGTH: 20
<212> TYPE: DNA
<213> ORGANISM: artificial sequence
<220> FEATURE:
<223> OTHER INFORMATION: primer sequence

<400> SEQUENCE: 25
atggtggatg gcatgatgtt                                              20

<210> SEQ ID NO 26
<211> LENGTH: 20
<212> TYPE: DNA
<213> ORGANISM: artificial sequence
<220> FEATURE:
<223> OTHER INFORMATION: primer sequence

<400> SEQUENCE: 26
tggaggttga ccatgctagg                                              20

<210> SEQ ID NO 27
<211> LENGTH: 21
<212> TYPE: DNA
<213> ORGANISM: artificial sequence
<220> FEATURE:
<223> OTHER INFORMATION: primer sequence

<400> SEQUENCE: 27
tagtgagatg ggcgggagtc t                                            21

<210> SEQ ID NO 28
<211> LENGTH: 17
<212> TYPE: DNA
<213> ORGANISM: artificial sequence
<220> FEATURE:
<223> OTHER INFORMATION: primer sequence

<400> SEQUENCE: 28
cctagtggat aaactgc                                                 17

<210> SEQ ID NO 29
<211> LENGTH: 19
<212> TYPE: DNA
<213> ORGANISM: artificial sequence
<220> FEATURE:
<223> OTHER INFORMATION: primer sequence

<400> SEQUENCE: 29
```

-continued

```
cccacagtga tccgccttt                                                19

<210> SEQ ID NO 30
<211> LENGTH: 24
<212> TYPE: DNA
<213> ORGANISM: artificial sequence
<220> FEATURE:
<223> OTHER INFORMATION: primer sequence

<400> SEQUENCE: 30
gcttctctgt gatgataacc ccta                                          24

<210> SEQ ID NO 31
<211> LENGTH: 20
<212> TYPE: DNA
<213> ORGANISM: artificial sequence
<220> FEATURE:
<223> OTHER INFORMATION: primer sequence

<400> SEQUENCE: 31 tccgccttt gcagtttatc                                                20

<210> SEQ ID NO 32
<211> LENGTH: 16
<212> TYPE: DNA
<213> ORGANISM: artificial sequence
<220> FEATURE:
<223> OTHER INFORMATION: primer sequence

<400> SEQUENCE: 32
tgtccctagt gagatg                                                   16

<210> SEQ ID NO 33
<211> LENGTH: 18
<212> TYPE: DNA
<213> ORGANISM: artificial sequence
<220> FEATURE:
<223> OTHER INFORMATION: primer sequence

<400> SEQUENCE: 33
tggcggacga cgacttgt                                                 18

<210> SEQ ID NO 34
<211> LENGTH: 21
<212> TYPE: DNA
<213> ORGANISM: artificial sequence
<220> FEATURE:
<223> OTHER INFORMATION: primer sequence

<400> SEQUENCE: 34
cgagcagacc gccgtgtact t                                             21

<210> SEQ ID NO 35
<211> LENGTH: 19
<212> TYPE: DNA
<213> ORGANISM: artificial sequence
<220> FEATURE:
<223> OTHER INFORMATION: primer sequence

<400> SEQUENCE: 35
aaagtttgga ggctgccgt                                                19

<210> SEQ ID NO 36
<211> LENGTH: 20
<212> TYPE: DNA
```

```
<213> ORGANISM: artificial sequence
<220> FEATURE:
<223> OTHER INFORMATION: primer sequence

<400> SEQUENCE: 36
tgttcggttc cctctaccaa                                              20

<210> SEQ ID NO 37
<211> LENGTH: 24
<212> TYPE: DNA
<213> ORGANISM: artificial sequence
<220> FEATURE:
<223> OTHER INFORMATION: primer sequence

<400> SEQUENCE: 37
cacagaaccg tcgcttcagc aaca                                         24

<210> SEQ ID NO 38
<211> LENGTH: 22
<212> TYPE: DNA
<213> ORGANISM: artificial sequence
<220> FEATURE:
<223> OTHER INFORMATION: primer sequence

<400> SEQUENCE: 38
caacatccat caccttgact ga                                           22

<210> SEQ ID NO 39
<211> LENGTH: 80
<212> TYPE: DNA
<213> ORGANISM: Artificial Sequence
<220> FEATURE:
<223> OTHER INFORMATION: Zinc Finger Binding Sequence

<400> SEQUENCE: 39
attttacaat cctgtcccta gtgagatggg cgggagtctt caatcctgtc cctagtggat  60
aaactgcaaa aggcggatca                                              80

<210> SEQ ID NO 40
<211> LENGTH: 80
<212> TYPE: DNA
<213> ORGANISM: artificial sequence
<220> FEATURE:
<223> OTHER INFORMATION: Complementary sequence of Zinc Finger binding
      sequence

<400> SEQUENCE: 40
taaaatgtta ggacagggat cactctaccc gccctcagaa gttaggacag ggatcaccta  60
tttgacgttt tccgcctagt                                              80

<210> SEQ ID NO 41
<211> LENGTH: 248
<212> TYPE: DNA
<213> ORGANISM: artificial sequence
<220> FEATURE:
<223> OTHER INFORMATION: reference sequence for ZFN binding

<400> SEQUENCE: 41
ccttgggatt tcagttggta ggttaaaaat gggagtggca tggagaggaa ataacagagg  60
ccctccagca atagcttctc tgtgatgata acccctatac tctatatttt acaatcctgt 120
ccctagtgag atgggcggga gtcttcaatc ctgtccctag tggataaact gcaaaaggcg 180
gatcactgtg gggtggcata aaagagaact cctagatgaa tgtctgccag gtaaacaaca 240
```

```
<210> SEQ ID NO 42
<211> LENGTH: 236
<212> TYPE: DNA
<213> ORGANISM: artificial sequence
<220> FEATURE:
<223> OTHER INFORMATION: Sequenced fragment showing ZFN cleavage

<400> SEQUENCE: 42
ccttgggatt tcagttggta ggttaaaaat gggagtggca tggagaggaa ataacagagg     60
ccctccagca atagcttctc tgtgatgata acccctatac tctatatttt acaatcctgt    120
ccctagatgg gcgggagtct tcaatcctgt ccctagtgga taaactgcaa aaggcggatc    180
actgtggggt ggcataaaag agaactccta gatgaatgtc tgccaggtaa acaaca        236

<210> SEQ ID NO 43
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 43
ccttgggatt tcagttggta ggttaaaaat gggagtggca tggagaggaa ataacagagg     60
ccctccagca atagcttctc tgtgatgata acccctatac tctatatttt acaatcctgt    120
ccctagtggg cgggagtctt caatcctgtc cctagtggat aaactgcaaa aggcggatca    180
ctgtggggtg gcataaaaga gaactcctag atgaatgtct gccaggtaaa caacagttga    240
ctta                                                                  244

<210> SEQ ID NO 44
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 44
ccttgggatt tcagttggta ggttaaaaat gggagtggca tggagaggaa ataacagagg     60
ccctccagca atagcttctc tgtgatgata acccctatac tctatatttt acaatcctgt    120
ccctagtggg cgggagtctt caatcctgtc cctagtggat aaactgcaaa aggcggatca    180
ctgtggggtg gcataaaaga gaactcctag atgaatgtct gccaggtaaa caacagttga    240
ctt                                                                   243

<210> SEQ ID NO 45
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 45
ccttgggatt tcagttggta ggttaaaaat gggagtggca tggagaggaa ataacagagg     60
ccctccagca atagcttctc tgtgatgata acccctatac tctatatttt acaatcctgt    120
ccctagtatg ggcgggagtc ttcaatcctg tccctagtgg ataaactgca aaaggcggat    180
cactgtgggg tggcataaaa agagaactcct agatgaatgt ctgccaggta acaacagtt    240 gact                                                                  244
```

<210> SEQ ID NO 46
<211> LENGTH: 241
<212> TYPE: DNA
<213> ORGANISM: artificial sequence
<220> FEATURE:
<223> OTHER INFORMATION: Sequenced fragment showing ZFN cleavage

<400> SEQUENCE: 46

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagtggg cgggagtctt caatcctgtc cctagtggat aaactgcaaa aggcggatca     180
ctgtgggtg gcataaaaga gaactcctag atgaatgtct gccaggtaaa caacagttga     240
c                                                                     241
```

<210> SEQ ID NO 47
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 47

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagatgg gcgggagtct tcaatcctgt cctagtggat aaactgcaa aaggcggatc     180
actgtggggt ggcataaaag agaactccta gatgaatgtc tgccaggtaa acaacagctg     240
actt                                                                  244
```

<210> SEQ ID NO 48
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 48

```
ccttgggatt tcagttggta ggttaaaaat gggagtggca tggagaggaa ataacagagg      60
ccctccagca atagcttctc tgtgatgata acccctatac tctatatttt acaatcctgt     120
cgggagtctt caatcctgtc cctagtggat aaactgcaaa aggcggatca ctgtggggtg     180
gcataaaaga gaactcctag atgaatgtct gccaggtaaa caacagttga cttaggactt     240
gat                                                                   243
```

<210> SEQ ID NO 49
<211> LENGTH: 235
<212> TYPE: DNA
<213> ORGANISM: artificial sequence
<220> FEATURE:
<223> OTHER INFORMATION: Sequenced fragment showing ZFN cleavage

<400> SEQUENCE: 49

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagatgg gcgggagtct tcaatcctgt cctagtgga taaactgcaa aaggcggatc     180
actgtggggt ggcataaaag agaactccta gatgaatgtc tgccaggtaa acaac         235
```

<210> SEQ ID NO 50
<211> LENGTH: 242
<212> TYPE: DNA
<213> ORGANISM: artificial sequence
<220> FEATURE:
<223> OTHER INFORMATION: Sequenced fragment showing ZFN cleavage

<400> SEQUENCE: 50
ccttgggatt tcagttggta ggttaaaaat gggagtggca tggagaggaa ataacagagg      60
ccctccagca atagcttctc tgtgatgata acccctatac tctatatttt acaatcctgt     120
ccctagggcg ggagtcttca atcctgtccc tagtggataa actgcaaaag gcggatcact     180
gtggggtggc ataaaagaga actcctagat gaatgtctgc caggtaaaca acagttgact     240
ta                                                                    242

<210> SEQ ID NO 51
<211> LENGTH: 242
<212> TYPE: DNA
<213> ORGANISM: artificial sequence
<220> FEATURE:
<223> OTHER INFORMATION: Sequenced fragment showing ZFN cleavage

<400> SEQUENCE: 51
ccttgggatt tcagttggta ggttaaaaat gggagtggca tggagaggaa ataacagagg      60
ccctccagca atagcttctc tgtgatgata acccctatac tctatatttt acaatcctgt     120
ccctatgggc gggagtcttc aatcctgtcc ctagtggata aactgcaaaa ggcggatcac     180
tgtggggtgg cataaaagag aactcctaga tgaatgtctg ccaggtaaac aacagttgac     240
tt                                                                    242

<210> SEQ ID NO 52
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 52
ccttgggatt tcagttggta ggttaaaaat gggagtggca tggagaggaa ataacagagg      60
ccctccagca atagcttctc tgtgatgata acccctatac tctatatttt acaatcctgt     120
ccctagggcg ggagtcttca atcctgtccc tagtggataa actgcaaaag gcggatcact     180
gtggggtggc ataaaagaga actcctagat gaatgtctgc caggtaaaca acagttgact     240
tag                                                                   243

<210> SEQ ID NO 53
<211> LENGTH: 242
<212> TYPE: DNA
<213> ORGANISM: artificial sequence
<220> FEATURE:
<223> OTHER INFORMATION: Sequenced fragment showing ZFN cleavage

<400> SEQUENCE: 53
ccttgggatt tcagttggta ggttaaaaat gggagtggca tggagaggaa ataacagagg      60
ccctccagca atagcttctc tgtgatgata acccctatac tctatatttt acaatcctgt     120
ccctagtggg cgggagtctt caatcctgtc cctagtggat aaactgcaaa aggcggatca     180
ctgtggggtg gcataaaaga gaactcctag atgaatgtct gccaggtaaa caacagttga     240
ct                                                                    242

<210> SEQ ID NO 54
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 54
ccttgggatt tcagttggta ggttaaaaat gggagtggca tggagaggaa ataacagagg      60
ccctccagca atagcttctc tgtgatgata acccctatac tctatatttt acaatcctgt     120
ccctagatgg gcgggagtct tcaatcctgt ccctagtgga taaactgcaa aaggcggatc     180
actgtggggt ggcataaaag agaactccta gatgaatgtc tgccaggtaa acaacagttg     240
actt                                                                 244

<210> SEQ ID NO 55
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 55
ccttgggatt tcagttggta ggttaaaaat gggagtggca tggagaggaa ataacagagg      60
ccctccagca atagcttctc tgtgatgata acccctatac tctatatttt acaatcctgt     120
ccctaatggg cgggagtctt caatcctgtc cctagtggat aaactgcaaa aggcggatca     180
ctgtggggtg gcataaaaga gaactcctag atgaatgtct gccaggtaaa caacagttga     240
ctta                                                                 244

<210> SEQ ID NO 56
<211> LENGTH: 235
<212> TYPE: DNA
<213> ORGANISM: artificial sequence
<220> FEATURE:
<223> OTHER INFORMATION: Sequenced fragment showing ZFN cleavage

<400> SEQUENCE: 56
ccttgggatt tcagttggta ggttaaaaat gggagtggca tggagaggaa ataacagagg      60
ccctccagca atagcttctc tgtgatgata acccctatac tctatatttt acaatcctgt     120
ccctagtggg cgggagtctt caatcctgtc cctagtggat aaactgcaaa aggcggatca     180
ctgtggggtg gcataaaaga gaactcctag atgaatgtct gccaggtaaa caaca          235

<210> SEQ ID NO 57
<211> LENGTH: 234
<212> TYPE: DNA
<213> ORGANISM: artificial sequence
<220> FEATURE:
<223> OTHER INFORMATION: Sequenced fragment showing ZFN cleavage

<400> SEQUENCE: 57
ccttgggatt tcagttggta ggttaaaaat gggagtggca tggagaggaa ataacagagg      60
ccctccagca atagcttctc tgtgatgata acccctatac tctatatttt acaatcctgt     120
ccctagatgg gcgggagtct tcaatcctgt ccctagtgga taaactgcaa aaggcggatc     180 actgtgggt ggcataaaag agaactccta gatgaatgtc tgccaggtaa acaa            234

<210> SEQ ID NO 58

<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 58

```
ccttgggatt tcagttggta ggttaaaaat gggagtggca tggagaggaa ataacagagg    60
ccctccagca atagcttctc tgtgatgata acccctatac tctatatttt acaatcctgt   120
ccctgggcgg gagtcttcaa tcctgtccct agtggataaa ctgcaaaagg cggatcactg   180
tggggtggca taaaagagaa ctcctagatg aatgtctgcc aggtaaacaa cagttgactt   240
agga                                                               244
```

<210> SEQ ID NO 59
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 59

```
ccttgggatt tcagttggta ggttaaaaat gggagtggca tggagaggaa ataacagagg    60
ccctccagca atagcttctc tgtgatgata acccctatac tctatatttt acaatcctgg   120
gcgggagtct tcaatcctgt ccctagtgga taaactgcaa aaggcggatc actgtggggt   180
ggcataaaag agaactccta gatgaatgtc tgccaggtaa acaacagttg acttaggact   240
tgat                                                               244
```

<210> SEQ ID NO 60
<211> LENGTH: 234
<212> TYPE: DNA
<213> ORGANISM: artificial sequence
<220> FEATURE:
<223> OTHER INFORMATION: Sequenced fragment showing ZFN cleavage

<400> SEQUENCE: 60

```
ccttgggatt tcagttggta ggttaaaaat gggagtggca tggagaggaa ataacagagg    60
ccctccagca atagcttctc tgtgatgata acccctatac tctatatttt acaatcctgt   120
ccctatgggc gggagtcttc aatcctgtcc ctagtggata aactgcaaaa ggcggatcac   180
tgtggggtgg cataaaagag aactcctaga tgaatgtctg ccaggtaaac aaca         234
```

<210> SEQ ID NO 61
<211> LENGTH: 241
<212> TYPE: DNA
<213> ORGANISM: artificial sequence
<220> FEATURE:
<223> OTHER INFORMATION: Sequenced fragment showing ZFN cleavage

<400> SEQUENCE: 61

```
ccttgggatt tcagttggta ggttaaaaat gggagtggca tggagaggaa ataacagagg    60
ccctccagca atagcttctc tgtgatgata acccctatac tctatatttt acaatcctgt   120
ccctaatggg cgggagtctt caatcctgtc cctagtggat aaactgcaaa aggcggatca   180
ctgtggggtg gcataaaaga gaactcctag atgaatgtct gccaggtaaa caacagttga   240
c                                                                  241
```

<210> SEQ ID NO 62
<211> LENGTH: 230

```
<212> TYPE: DNA
<213> ORGANISM: artificial sequence
<220> FEATURE:
<223> OTHER INFORMATION: Sequenced fragment showing ZFN cleavage

<400> SEQUENCE: 62
ccttgggatt tcagttggta ggttaaaaat gggagtggca tggagaggaa ataacagagg    60
ccctccagca atagcttctc tgtgatgata acccctatac tctatatttt acaatcctgt   120
ccctagatgg gcgggagtct tcaatcctgt ccctagtgga taaactgcaa aaggcggatc   180
actgtggggt ggcataaaag agaactccta gatgaatgtc tgccaggtaa              230

<210> SEQ ID NO 63
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 63
ccttgggatt tcagttggta ggttaaaaat gggagtggca tggagaggaa ataacagagg    60
ccctccagca atagcttctc tgtgatgata acccctatac tctatatttt acaatcctgt   120
ccctatgggc gggagtcttc aatcctgtcc ctagtggata aactgcaaaa ggcggatcac   180
tgtggggtgg cataaaagag aactcctaga tgaatgtctg ccaggtaaac aacagttgac   240
tta                                                                 243

<210> SEQ ID NO 64
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 64
ccttgggatt tcagttggta ggttaaaaat gggagtggca tggagaggaa ataacagagg    60
ccctccagca atagcttctc tgtgatgata acccctatac tctatatttt acaatcctgt   120
ccctagggcg ggagtcttca atcctgtccc tagtggataa actgcaaaag gcggatcact   180
gtggggtggc ataaaagaga actcctagat gaatgtctgc caggtaaaca acagttgact   240
tagg                                                                244

<210> SEQ ID NO 65
<211> LENGTH: 239
<212> TYPE: DNA
<213> ORGANISM: artificial sequence
<220> FEATURE:
<223> OTHER INFORMATION: Sequenced fragment showing ZFN cleavage

<400> SEQUENCE: 65
ccttgggatt tcagttggta ggttaaaaat gggagtggca tggagaggaa ataacagagg    60
ccctccagca atagcttctc tgtgatgata acccctatac tctatatttt acaatcctgt   120
ccctatgggc gggagtcttc aatcctgtcc ctagtggata aactgcaaaa ggcggatcac   180
tgtggggtgg cataaaagag aactcctaga tgaatgtctg ccaggtaaac aacagttga    239

<210> SEQ ID NO 66
<211> LENGTH: 237
<212> TYPE: DNA
<213> ORGANISM: artificial sequence
<220> FEATURE:
```

<223> OTHER INFORMATION: Sequenced fragment showing ZFN cleavage

<400> SEQUENCE: 66

```
ccttgggatt tcagttggta ggttaaaaat gggagtggca tggagaggaa ataacagagg    60
ccctccagca atagcttctc tgtgatgata acccctatac tctatatttt acaatcctgt   120
cccttgggcg ggagtcttca atcctgtccc tagtggataa actgcaaaag gcggatcact   180
gtggggtggc ataaaagaga actcctagat gaatgtctgc caggtaaaca acagttg      237
```

<210> SEQ ID NO 67
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 67

```
ccttgggatt tcagttggta ggttaaaaat gggagtggca tggagaggaa ataacagagg    60
ccctccagca atagcttctc tgtgatgata acccctatac tctatatttt acaatcctgt   120
ccctagtgag atgggcggga gtcttcaatc ctgtccctag ataaactgca aaaggcggat   180
cactgtgggg tggcataaaa gagaactcct agatgaatgt ctgccaggta cacaacagtt   240
gac                                                                 243
```

<210> SEQ ID NO 68
<211> LENGTH: 237
<212> TYPE: DNA
<213> ORGANISM: artificial sequence
<220> FEATURE:
<223> OTHER INFORMATION: Sequenced fragment showing ZFN cleavage

<400> SEQUENCE: 68

```
ccttgggatt tcagttggta ggttaaaaat gggagtggca tggagaggaa ataacagagg    60
ccctccagca atagcttctc tgtgatgata acccctatac tctatatttt acaatcctgt   120
ccctagtgag atgggcggga gtcttcaatc ctgtccctag ataaactgca aaaggcggat   180
cactgtgggg tggcataaaa gagaactcct agatgaatgt ctgccaggta aacaaca      237
```

<210> SEQ ID NO 69
<211> LENGTH: 241
<212> TYPE: DNA
<213> ORGANISM: artificial sequence
<220> FEATURE:
<223> OTHER INFORMATION: Sequenced fragment showing ZFN cleavage

<400> SEQUENCE: 69

```
ccttgggatt tcagttggta ggttaaaaat gggagtggca tggagaggaa ataacagagg    60
ccctccagca atagcttctc tgtgatgata acccctatac tctatatttt acaatcctgt   120
ccctagtgag atgggcggga gtcttcaatc ctgtccctag aaactgcaaa aggcggatca   180
ctgtggggtg gcataaaaga gaactcctag atgaatgtct gccaggtaaa caacagctga   240
c                                                                   241
```

<210> SEQ ID NO 70
<211> LENGTH: 235
<212> TYPE: DNA
<213> ORGANISM: artificial sequence
<220> FEATURE:
<223> OTHER INFORMATION: Sequenced fragment showing ZFN cleavage

<400> SEQUENCE: 70

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag aaactgcaaa aggcggatca     180
ctgtggggtg gcataaaaga gaactcctag atgaatgtct gccaggtaaa caaca          235
```

<210> SEQ ID NO 71
<211> LENGTH: 223
<212> TYPE: DNA
<213> ORGANISM: artificial sequence
<220> FEATURE:
<223> OTHER INFORMATION: Sequenced fragment showing ZFN cleavage

<400> SEQUENCE: 71

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag aaactgcaaa aggcggatca     180
ctgtggggtg gcataaaaga gaactcctag atgaatgtct gcc                       223
```

<210> SEQ ID NO 72
<211> LENGTH: 241
<212> TYPE: DNA
<213> ORGANISM: artificial sequence
<220> FEATURE:
<223> OTHER INFORMATION: Sequenced fragment showing ZFN cleavage

<400> SEQUENCE: 72

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctgc aaaaggcgga tcactgtggg     180
gtggcataaa agagaactcc tagatgaatg tctgccaggt aaacaacagt tgacttagga     240
c                                                                     241
```

<210> SEQ ID NO 73
<211> LENGTH: 222
<212> TYPE: DNA
<213> ORGANISM: artificial sequence
<220> FEATURE:
<223> OTHER INFORMATION: Sequenced fragment showing ZFN cleavage

<400> SEQUENCE: 73

```
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag ttaaactgca aaaggcggat     180
cactgtgggg tggcataaaa gagaaatcct agatgaatgt ct                        222
```

<210> SEQ ID NO 74
<211> LENGTH: 235
<212> TYPE: DNA
<213> ORGANISM: artificial sequence
<220> FEATURE:
<223> OTHER INFORMATION: Sequenced fragment showing ZFN cleavage

<400> SEQUENCE: 74

```
ccttgggatt tcagttggta ggttaaaaat gggagtggca tggagaggaa ataacagagg      60
ccctccagca atagcttctc tgtgatgata acccctatac tctatatttt acaatcctgt     120
```

```
ccctagtgag atgggcggga gtcttcaatc ctgtccctag aaactgcaaa aggcggatca    180
ctgtggggtg gcataaaaga gaactcctag atgaatgtct tccaggtaaa caaca         235
```

<210> SEQ ID NO 75
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 75

```
ccttgggatt tcagttggta ggttaaaaat gggagtggca tggagaggaa ataacagagg    60
ccctccagca atagcttctc tgtgatgata acccctatac tctatatttt acaatcctgt   120
ccctagtgag atgggcggga gtcttcaatc ctgtccctag ataaactgca aaaggcggat   180
cactgtgggg tggcataaaa gagaactcct agatgaatgt ctgccaggta aacaacagtt   240
gac                                                                  243
```

<210> SEQ ID NO 76
<211> LENGTH: 242
<212> TYPE: DNA
<213> ORGANISM: artificial sequence
<220> FEATURE:
<223> OTHER INFORMATION: Sequenced fragment showing ZFN cleavage

<400> SEQUENCE: 76

```
ccttgggatt tcagttggta ggttaaaaat gggagtggca tggagaggaa ataacagagg    60
ccctccagca atagcttctc tgtgatgata accccctatac tctatatttt acaatcctgt  120
ccctagtgag atgggcggga gtcttcaatc ctgtccctag aaactgcaaa aggcggatca   180
ctgtggggtg gcataaaaga gaactcctag atgaatgact gccaggtaaa caacagttga   240
ct                                                                   242
```

<210> SEQ ID NO 77
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 77

```
ccttgggatt tcagttggta ggttaaaaat gggagtggca tggagaggaa ataacagagg    60
ccctccagca atagcttctc tgtgatgata accccctatac tctatatttt acaatcctgt  120
ccctagtgag atgggcggga gtcttcaatc ctgtccctag aaactgcaaa aggcggatca   180
ctgtggggtg gcataaaaga gaactcctag atgaatgtct gccaggtaaa caacagttga   240
ctta                                                                 244
```

<210> SEQ ID NO 78
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 78

```
ccttgggatt tcagttggta ggttaaaaat gggagtggca tggagaggaa ataacagagg    60
ccctccagca atagcttctc tgtgatgata acccttatac tctatatttt acaatcctgt   120
ccctagtgag atgggcggga gtcttcaatc ctgtccctag ataaactgca aaaggcggat   180
```

```
cactgtgggg tggcataaaa gagaactcct agatgaatgt ctgccaggta aacaacagtt    240
gac                                                                 243
```

<210> SEQ ID NO 79
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 79

```
ccttgggatt tcagttggta ggttaaaaat gggagtggca tggagaggaa ataacagagg     60
ccctccagca atagcttctc tgtgatgata acccctatac tctatatttt acaatcctgt    120
ccctagtgag atgggcggga gtcttcaatc ctgtccctag ataaactgca aaaggcggat    180
cactgtgggg tggcctaaaa gagaactcct agatgaatgt ctgccaggta aacaacagtt    240
gac                                                                 243
```

<210> SEQ ID NO 80
<211> LENGTH: 236
<212> TYPE: DNA
<213> ORGANISM: artificial sequence
<220> FEATURE:
<223> OTHER INFORMATION: Sequenced fragment showing ZFN cleavage

<400> SEQUENCE: 80

```
ccttgggatt tcagttggta ggttaaaaat gggagtggca tggagaggaa ataacagagg     60
ccctccagca atagcttctc tgtgatgata acccctatac tctatatttt acaatcctgt    120
ccctagtgag atgggcggga gtcttcaatc ctgtccctag ataaactgca aaaggcggat    180
cactgtgggg tggcataaaa gagaactcct agatgaatgt ctgccaggta aacaac        236
```

<210> SEQ ID NO 81
<211> LENGTH: 238
<212> TYPE: DNA
<213> ORGANISM: artificial sequence
<220> FEATURE:
<223> OTHER INFORMATION: Sequenced fragment showing ZFN cleavage

<400> SEQUENCE: 81

```
ccttgggatt tcagttggta ggttaaaaat gggagtggca tggagaggaa ataacagagg     60
ccctccagca atagcttctc tgtgatgata acccctatac tctatatttt acaatcctgt    120
ccctagtgag atgggcggga gtcttcaatc ctgtccctag ataaactgca aaaggcggat    180
cactgtgggg tggcataaaa gagaactcct agatgaatgt ctgccaggta aacaacag     238
```

<210> SEQ ID NO 82
<211> LENGTH: 237
<212> TYPE: DNA
<213> ORGANISM: artificial sequence
<220> FEATURE:
<223> OTHER INFORMATION: Sequenced fragment showing ZFN cleavage

<400> SEQUENCE: 82

```
ccttgggatt tcagttggta ggttaaaaat gggagtggca tggagaggaa ataacagagg     60
ccctccagca atagcttctc tgtgatgata acccctatac tctatatttt acaatcctgt    120
ccctagtgag atgggcggga gtcttcaatc ctgtccctag aaactgcaaa aggcggatca    180
ctgtggggtg gcataaaaga gaactcctag atgaatgtct gccaggtaaa caacagt      237
```

<210> SEQ ID NO 83
<211> LENGTH: 237
<212> TYPE: DNA
<213> ORGANISM: artificial sequence
<220> FEATURE:
<223> OTHER INFORMATION: Sequenced fragment showing ZFN cleavage

<400> SEQUENCE: 83
ccttgggatt tcagttggta ggttaaaaat gggagtggca tggggaggaa ataacagagg      60
ccctccagca atagcttctc tgtgatgata acccctatac tctatatttt acaatcctgt     120
ccctagtgag atgggcggga gtcttcaatc ctgtccctag ttaaactgca aaaggcggat     180
cactgtgggg tggcataaaa gagaactcct agatgaatgt ctgccaggta aacaaca       237

<210> SEQ ID NO 84
<211> LENGTH: 237
<212> TYPE: DNA
<213> ORGANISM: artificial sequence
<220> FEATURE:
<223> OTHER INFORMATION: Sequenced fragment showing ZFN cleavage

<400> SEQUENCE: 84
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag ttaaactgca aaaggcggat     180
cactgtgggg tggcataaaa gagaactcct agatgaatgt ctgccaggta aacaaca       237

<210> SEQ ID NO 85
<211> LENGTH: 237
<212> TYPE: DNA
<213> ORGANISM: artificial sequence
<220> FEATURE:
<223> OTHER INFORMATION: Sequenced fragment showing ZFN cleavage

<400> SEQUENCE: 85
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag ttaaactgca aaaggcggat     180
cactgtgggg tggcataaaa gagaaatccc agatgaatgt ctgccaggta aacaaca       237

<210> SEQ ID NO 86
<211> LENGTH: 225
<212> TYPE: DNA
<213> ORGANISM: artificial sequence
<220> FEATURE:
<223> OTHER INFORMATION: Sequenced fragment showing ZFN cleavage

<400> SEQUENCE: 86
ccttgggatt tcagttggta ggttaaaaat gggagtggca tggagaggaa ataacagagg      60
ccctccagca atagcttctc tgtgatgata acccctatac tctatatttt acaatcctgt     120
ccctagtgag atgggcggga gtcttcaatc ctgtccctag taaactgcaa aaggcggatc     180 actgtgggt ggcataaaag agaactccta gatgaatgtc tgcca                     225

<210> SEQ ID NO 87
<211> LENGTH: 243
<212> TYPE: DNA
<213> ORGANISM: artificial sequence
<220> FEATURE:
<223> OTHER INFORMATION: Sequenced fragment showing ZFN cleavage

<400> SEQUENCE: 87

```
ccttgggatt tcagttggta ggttaaaaat gggagtggca tggagaggaa ataacagagg    60
ccctccagca atagcttctc tgtgatgata accectatac tctatatttt acaatcctgt   120
ccctagtgag atgggcggga gtcttcaatc ctgtccctag aaactgcaaa aggcggatca   180
ctgtggggtg gcataaaaga gaactcctag atgaatgtct gccaggtaaa caacagttga   240
ctt                                                                 243
```

<210> SEQ ID NO 88
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 88

```
ccttgggatt tcagttggta ggttaaaaat gggagtggca tggagaggaa ataacagagg    60
ccctccagca atagcttctc tgtgatgata accectatac tctatacttt acaatcctgt   120
ccctagtgag atgggcggga gtcttcaatc ctgtccctag ataaactgca aaaggcggat   180
cactgtgggg tggcataaaa gagaactcct agatgaatgt ctgccaggta aacaacagtt   240
gact                                                                244
```

<210> SEQ ID NO 89
<211> LENGTH: 244
<212> TYPE: DNA
<213> ORGANISM: artificial sequence
<220> FEATURE:
<223> OTHER INFORMATION: Sequenced fragment showing ZFN cleavage

<400> SEQUENCE: 89

```
ccttgggatt tcagttggta ggttaaaaat gggagtggca tggagaggaa ataacagagg    60
ccctccagca atagcttctc tgtgatgata accectatac tctatatttt acaatcctgt   120
ccctagtgag atgggcggga gtcttcaatc ctgtccctag ttaaactgca aaaggcggat   180
cactgtgggg tggcataaaa gagaactcct agatgaatgt ctgccaggta aacaacagtt   240
gact                                                                244
```

<210> SEQ ID NO 90
<211> LENGTH: 238
<212> TYPE: DNA
<213> ORGANISM: artificial sequence
<220> FEATURE:
<223> OTHER INFORMATION: Sequenced fragment showing ZFN cleavage

<400> SEQUENCE: 90

```
ccttgggatt tcagttggta ggttaaaaat gggagtggca tggagaggaa ataacagagg    60
ccctccagca atagcttctc tgtgatgata accectatac tctatatttt acaatcctgt   120
ccctagtgag atgggcggga gtcttcaatc ctgtccctag ttaaactgca aaaggcggat   180
cactgtgggg tggcataaaa gagaactcct agatgaatgt ctgccaggta aacaacag    238
```

<210> SEQ ID NO 91
<211> LENGTH: 226
<212> TYPE: DNA
<213> ORGANISM: artificial sequence
<220> FEATURE:
<223> OTHER INFORMATION: Sequenced fragment showing ZFN cleavage

```
<400> SEQUENCE: 91
ccttgggatt tcagttggta ggttaaaaat gggagtggca tggagaggaa ataacagagg          60
ccctccagca atagcttctc tgtgatgata acccctatac tctatatttt acaatcctgt         120
ccctagtgag atgggcggga gtcttcaatc ctgtccctag ttaaactgca aaaggcggat         180
cactgtgggg tggcataaaa gagaactcct agatgaatgt ctgcca                       226
```